(12) United States Patent
Asako et al.

(10) Patent No.: US 6,884,607 B2
(45) Date of Patent: Apr. 26, 2005

(54) PROCESS FOR PRODUCING OPTICALLY ACTIVE 4-HALO-3-HYDROXYBUTANOATE

(75) Inventors: Hiroyuki Asako, Toyonaka (JP); Kenji Matsumura, Toyonaka (JP); Masatoshi Shimizu, Toyonaka (JP); Nobuya Itoh, Toyama (JP); Ryuhei Wakita, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 249 days.

(21) Appl. No.: 10/004,115

(22) Filed: Dec. 6, 2001

(65) Prior Publication Data

US 2003/0134402 A1 Jul. 17, 2003

(30) Foreign Application Priority Data

| Dec. 7, 2000 | (JP) | 2000-372704 |
| Jan. 15, 2001 | (JP) | 2001-006144 |
| Feb. 2, 2001 | (JP) | 2001-026594 |
| Jun. 11, 2001 | (JP) | 2001-175175 |

(51) Int. Cl.$^7$ .............. C12N 9/02; C12N 9/04; C12N 1/21; C12N 15/52; C07N 21/04

(52) U.S. Cl. ........ 435/189; 435/69.7; 435/190; 435/252.3; 435/252.33; 435/254.11; 435/320.1; 435/471; 536/23.2; 536/23.4

(58) Field of Search .............. 435/189, 69.7, 435/190, 252.3, 252.33, 254.11, 254.5, 320.1, 471; 536/23.2, 23.4, 23.7

(56) References Cited

U.S. PATENT DOCUMENTS

| 4,895,979 A | 1/1990 | Noyori et al. |
| 4,978,768 A | 12/1990 | von der Crone |
| 5,523,223 A | 6/1996 | Kula et al. |
| 5,559,030 A | 9/1996 | Matsuyama et al. |
| 5,908,953 A | 6/1999 | Matsuda et al. |
| 6,218,156 B1 | 4/2001 | Yasohara et al. |
| 6,312,933 B1 | 11/2001 | Kimoto et al. |

FOREIGN PATENT DOCUMENTS

| EP | 0 606 899 A2 | 7/1994 |
| EP | 0 967 271 A1 | 12/1999 |
| EP | 1201647 A2 | 5/2000 |
| EP | 1 013 758 A2 | 6/2000 |
| EP | 1 213 354 A3 | 2/2003 |
| JP | 60-199393 | 10/1985 |
| JP | 60-251890 A | 12/1985 |
| JP | 62 0259902 | 2/1987 |
| JP | 63-123387 A | 5/1988 |
| JP | 1-222787 A | 9/1989 |
| JP | 2566962 B2 | 10/1996 |
| JP | 10-94399 A | 4/1998 |
| WO | WO 93/18138 | 8/1993 |
| WO | WO 99/42590 | 8/1999 |
| WO | WO 00/71503 A1 | 11/2000 |

OTHER PUBLICATIONS

Book of Abstracts, 2000 International Chemical Congress of Pacific Basin Societies, Honolulu, Hawai, Dec. 14–19, 2000, Abstract 3Y7p7, p. 374 (WI translation).

Kataoka et al., "Stereoselective Reduction of Ethyl 4–Chloro 3–Oxobutanoate by *Escherichia Coli* Transformant Cells Coexpressing the Aldehyde Reductase and Glucose Dehydrogenase Genes," Appl. Microbiol Biotechnol 51 pp 486–490 199.

Database VBI Online: Oct. 17, 1998 Kamara. M Hubberena Zeae Gene for Reductase, Retrieved from EBI Database Accession No. AC014493.074646 P 002209648.

Database WPI, Week 198545, 1985, Derwent Publications Ltd., London GB; AN 1985–287883 XP–002209642.

Database CA Online—Chemica Abstracts Service Columbus, Ohio, US; Takahashi et al., "Microbial Production of D alphe amino Acids," Retrieved from STN Database Accession No. 107:76090 XP 002209641.

Itoh et al., Purification and Characterization of Phenylacetaldehyde Reductase and a Styrene–Assimilating Corynebacterium Strain, ST–10, Applied and Environmental Microbiology, pp 3783–3788 (Oct. 1997).

Itoh et al., Chiral alcohol production by NADH–dependent phenylacetaldehyde reductase coupled with in situ regeneration of NADH, Eur. J. Biochem., 269:2394–2402 (2002).

Itoh et al., Cloning, sequence analysis, and expression in *Escherichia coli* of the gene encoding phenylacetaldehyde reductase from styrene–assimilating Corynebacterium sp. strain SI–10, Appl Microbiol. Biotechnol. 52:386–392 (1999).

Itho et al., Production of chiral alcohols by enantioselective reduction with NADH–dependent phenylacetaldehyde reductase from Corynebacterium strain, ST–10, Journal Molecular Catalysis B:Enzymatic 6:41–50 (1999).

Troostwijk et al., Method for the Synthesis of 4–substituted Acetoacetates, Journal of the Chemical Society Chem. Comm. No. 23, pp. 932–933 (Dec. 7, 1977).

*Primary Examiner*—Elizabeth Slobodyansky
(74) *Attorney, Agent, or Firm*—Fitch, Even, Tabin & Flannery

(57) ABSTRACT

There are provided a polynucleotide sequence coding for an amino acid sequence capable of preferentially producing (S)-4-bromo-3-hydroxy-butanoate by asymmetrically reducing 4-bromo-3-oxobutanoate, A DNA construct having a promoter in operative linkage with the polynucleotide sequence, a recombinant vector containing the polynucleotide sequence, a transformant, a recombinant vector and the like.

17 Claims, No Drawings

PROCESS FOR PRODUCING OPTICALLY ACTIVE 4-HALO-3-HYDROXYBUTANOATE

BACKGROUND OF THE INVENTION

Optically active 4-halo-3-hydroxy butanoate and related compounds are known as a useful intermediate compounds for the production of pharmaceuticals and agrochemicals.

Various methods for optically active 4-halo-3-hydroxybutanoate and compounds derivatized therefrom have been known so far, however, these methods are not always satisfactory in yield or industrial applicability

SUMMARY OF THE INVENTION

According to the present invention, optically active 4-halo-3-hydroxy butanoate and related compounds can be readily obtained in an industrially desirable manner.

The present invention provides:

1 a polynucleotide sequence having:

a) a polynucleotide sequence coding for an amino acid sequence of SEQ ID NO: 1;

b) a polynucleotide sequence that hybridizes, under stringent conditions, with a polynucleotide sequence coding for an amino acid sequence of SEQ ID NO: 1, the amino acid sequence being an amino acid sequence of a protein capable of preferentially producing (S)-4-bromo-3-hydroxybutanoate by asymmetrically reducing 4-bromo-3-oxobutanoate; or c) a polynucleotide sequence of SEQ ID NO: 2 (hereinafter referred to as "the present gene or the present polynucleotide";

2. a protein having:

i) an amino acid sequence of SEQ ID NO: 1;

ii) an amino acid sequence encoded by a polynucleotide sequence that hybridizes under stringent conditions with a polynucleotide sequence of SEQ ID NO: 2 coding for an amino acid sequence of a protein capable of preferentially producing (S)-4-bromo-3-hydroxybutanoate by asymmetrically reducing 4-bromo-3-oxobutanoate; or iii) an amino acid sequence of SEQ ID NO: 1, wherein one or more amino acids are deleted, replaced or added, said amino acid sequence being an amino acid sequence of a protein capable of preferentially producing (S)-4-bromo-3-hydroxybutanoate by asymmetrically reducing 4-bromo-3-oxobutanoate (hereinafter referred to as "the present protein or enzyme");

3. a process for producing (S)-4-halo-3-hydroxybutanoate, which comprises reacting 4-halo-3-oxobutanoic acid ester with the protein as defined above, a transformant, which produces the protein or a treated product thereof.

4. a process for producing an optically active 3-hydroxybutanoate of formula (1a):

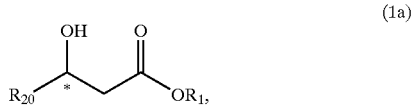

(1a)

wherein $R_1$ represents an alkyl group, and $R_{20}$ represents a methyl group which may be substituted with a halogen atom, which process comprises reacting 3-oxobutanoate of formula (2a):

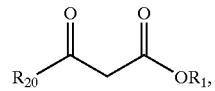

(2a)

wherein $R_1$ and $R_{20}$ represent the same as defined above, with a whole cells of a microorganism or a treated product thereof, which microorganism belongs to *Penicillium citrinum, Cryptcoccus humicolus*, or *Bacillus alvei* and is capable of asymmetrically reducing the oxo group at 3-position of the compound of formula (2a) to corresponding 3-hydroxy group;

5. a process for producing an optically active 4-bromo-3-hydroxybutanoate of formula (1b):

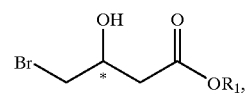

(1b)

wherein $R_1$ represents a (C2–C8)alkyl group, which process comprises reacting 4-bromo-3-oxobutanoate of formula (2b):

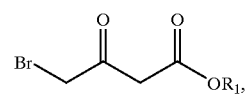

(2b)

wherein $R_1$ represents the same as defined above, with an enzyme having:

iv) all amino acid sequence of SEQ ID NO: 34;

v) an amino acid sequence encoded by a polynucleotide sequence that hybridizes, under stringent conditions, with a polynucleotide sequence of SEQ ID NO, 35, wherein the amino acid sequence is an ammo acid sequence of a protein capable of preferentially producing optically active 4-bromo-3-hydroxybutanoate by asymmetrically reducing 4-bromo-3-oxobutanoate; and vi) an amino acid sequence of SEQ ID NO: 34, wherein one or more amino acids are deleted, replaced or added, said amino acid sequence being an amino acid sequence of a protein capable of preferentially producing optically active 4-bromo-3-hydroxybutanoate by asymmetrically reducing 4-bromo-3-oxobutanoate (hereinafter referred to as "the instant enzyme"); and 6. A process for producing 4-cyano-3-hydroxybutanoic acid, which comprises reacting 4-bromo-3-hydroxybutanoic acid ester with a metal cyanide in the presence of an alkaline earth metal hydroxide and an alkaline earth metal halogenide.

DETAILED DESCRIPTION OF THE INVENTION

First, a description will be made to the first aspect of the present invention drawn to the present gene. The present gene may be a wild-type gene or an artificially produced gene by introducing a mutation through site-specific mutation introduction method and/or a mutagenic treatment as described below into the wild type-gene. The wild-type gene can be found out and obtained among microorganisms capable of preferentially producing (S)-4-bromo-3-hydroxybutanoate ester by asymmetrically reducing 4-bromo-3-oxo-butanoate ester. Examples of the microorganism include, for example, microorganisms belonging to the genus *Penicillium* such as *Penicillium citrinum*.

Examples of the present gene include, for example, polynucleotides shown above in a) to c) and the like.

The stringent conditions in b) above include conditions that are referred to in a Southern hybridization method as described, for example, in the "Cloning and Sequence" (supervised by K. Watanabe, edited by M. Sugiura and published from Noson Bunkasha Co., Ltd. in 1989). More specifically, examples of the polynucleotide include, for example, a polynucleotide that is defined by the following conditions: (1) the polynucleotide hybridizes with a polynucleotide coding for the amino acid sequence of SEQ ID NO: 1 to form a hybrid with the polynucleotide coding for the amino acid sequence of SEQ ID NO: 1 under high ion concentration conditions (e.g., 6×SSC (900 mM sodium chloride, 90 mM sodium citrate) at 65° C., and (2) the polynucleotide hybrid formed is maintained as a hybrid after being kept at 65° C. for 30 minutes under a low ion concentration (e. g. 6×SSC (15 mM sodium chloride and 1.5 mM of sodium citrate)

Examples of the present gene also includes, for example,
(d) a polynucleotide coding for an amino acid sequence of SEQ ID NO: 1 in which a part of the nucleotides is deleted, substituted or added; and
(e) a polynucleotide sequence having 80% or more sequence identity with the polynucleotide sequence coding for an amino acid sequence of SEQ ID NO: 1; and the like.

These polynucleotide sequences may be a polynucleotide obtained by cloning from the wild-type gene or may be a polynucleotide obtained from the cloned gene or a recombinant gene therefrom by artificially introducing partial deletion, substitution or addition of nucleotide(s) in the polynucleotide sequence coding for the amino acid sequence of SEQ ID NO: 1. Specific examples thereof include, for example, a polynucleotide sequence of SEQ ID NO: 2, and a polynucleotide sequence of SEQ ID NO: 28, and the like.

The polynucleotides a) to d) as defined above of the present invention can be prepared, for example, by preparing a cDNA library and conducting PCR (polymerase chain reaction) using the cDNA as a template and a suitable primer. The cDNA library can be prepared, for example, from microorganisms belonging to the genus Penicillium such as *Penicillium citrinum* according to genetic engineering methods (e.g. "A new cell engineering experiment protocol" (edited by the Cancer Research Unit, Medical Science Research Laboratory, the University of Tokyo, Shujinsha, Co., Ltd., 1993).

The polynucleotide sequence of SEQ ID NO: 28 can be amplified by carrying out PCR using the aforementioned cDNA library as a template and using an oligonucleotide sequence of SEQ ID NO: 23 and an oligonucleotide sequence of SEQ ID NO: 24 as primers Examples of the PCR conditions include, for example, a reaction condition in which a reaction mixture containing four types of dNTP, each of which are added so that the final concentration thereof in the mixture is 20 $\mu$M, 15 pmol of two types of oligonucleotide as primers, 1.3 U of Taqpolymerase and the cDNA library as a template is heated at 97° C. (for 2 minutes), 10 times of a cycle of reacting at 97° C. (for 0.25 minutes), 50° C. (for 0.5 minutes) and 72° C.(for 1.5 minutes), 20 times of a cycle of reacting at 97° C.(for 0.25 minutes), 55° C.(for 0.5 minutes) and 72° C. (for 2.5 minutes), and at 72° C. for 7 minutes.

A recognition sequence for a restriction enzyme may be added to the 5' terminal of the primer used for the PCR.

The present gene can also be prepared by PCR using the cDNA described above as a template and using, as primers, an oligonucleotide selected from a partial sequence of the polynucleotide sequence coding for the amino acid sequence of SEQ ID NO: 1(e.g. an oligonucleotide comprising about 14 or more nucleotides at the 5' terminal of the polynucleotide sequence coding for the amino acid sequence of SEQ ID NO: 1) and an oligonucleotide comprising about 14 or more nucleotides complement to a nucleotide sequence at the vicinity of DNA inserting site of the vector used for constructing the cDNA.

Cloning of the amplified polynucleotide into a vector can provide a recombinant vector suitably used for the present invention according to methods as disclosed in "Molecular Cloning: A Laboratory Manual 2nd edition" (1989), Cold Spring Harbor Laboratory Press, "Current Protocols in Molecular Biology" (1987), John Wiley & Sons, Inc. ISBN 0-471-50338-X, etc. Examples of the vector that may be used include, for example, pUC119 (Takara Shuzo Co., Ltd.), pTV118N (Takara Shuzo Co., Ltd.), pBluescriptII (Toyobo Co., Ltd.), pCR2.1-TOPO™ (Invitrogen Co., Ltd.), pTrc99A (Pharmacia) and pKK223-3 (Pharmacia).

Alternatively, the present gene can be obtained by hybdridizing a nucleotide sequence comprising about 15 or more nucleotides selected from the nucleotide sequence coding for the amino acid sequence of SEQ ID NO:1, as a probe, with the cDNA inserted into a vector derived from a microorganism or a phage, thereby detecting the desired DNA which specifically binds to the probe, under a hybridization conditions described below.

Colony hybridization or plaque hybridization can be employed as a method for hybridizing a probe with a chromosomal DNA or cDNA library, and can be selected in accordance with the type of the vector used for preparation of the library.

Colony hybridization is preferably used together with the library prepared from a plasmid vectors For example, the library DNA is introduced into a host microorganism to produce a transformant, and the transformant is diluted, the diluted product is inoculated on an agar plate, and incubated until a colony appears.

Plaque hybridization is preferably used together with the library DNA prepared from a phage vector. For example, a host microorganism is mixed with the phage having the library, the resulting mixture is mixed with a soft cultivation agar medium under suitable conditions for infection, the mixture is then placed on an agar plate and incubated until formation of a plaque is confirmed.

A membrane is placed on the surfaces of the cultivation agar medium obtained by the hybridization methods as described above, thereby the transformant or the phage is adsorbed onto the membrane to give a transcribed membrane, After this membrane is subjected to alkaline treatment, it is neutralized and the DNA is then immobilized on the membrane. More specifically, in the case of plaque hybridization, nitro cellulose membrane or nylon membrane (e.g. Hybond-N⁺ (registered trademark of Amasham Inc.)) is placed on the aforementioned cultivation agar medium and is left standing for about one minute so that the phage particle is adsorbed by the membrane. Then, the membrane is immersed in alkali solution (e.g. 1.5 M sodium chloride and 0.5M sodium hydroxide) for about three minutes until the phage particle is dissolved. After the phage DNA is eluted onto the membrane, it is immersed in a neutralization solution (e.g. 1.5 M sodium chloride and 0.5 M trishydrochloric acid buffer solution at pH 7.5) for about five minutes. Then, the membrane is washed with a solution (e.g.

0.3 M sodium chloride, 30 mM citric acid, 0.2 M tris-hydrochloric acid buffer solution at pH 7.5) for five minutes. Thereafter, it is heated at about 80° C. for about 90 minutes until the phage DNA is immobilized on the membrane.

Using the membrane prepared in the aforementioned steps, hybridization is performed with the DNA as a probe. Hybridization can be carried out according to the method disclosed, for example, in "Molecular Cloning: A Laboratory Manual 2nd edition (1989)" by J. Sambrook, E. F Frisch and T. Maniatis, Cold Spring Harbor Laboratory Press.

The DNA used as a probe can be labeled with either radioactive isotope or fluorophore. The probe DNA may be labeled, for example, by conducting PCR in which the dCTP in PCR reaction solution is replaced with (α-32P) dCTP using the Random Primer Labeling Kit (Takara Shuzo Co., Ltd.) and the probe DNA is used as a template. The labeling of the probe DNA with the fluorophore can be accomplished, for example, by ECL Direct Nucleic Acid Labeling and Detection System produced by Amasham, and the like.

For example, hybridization can be carried out as follows:

The membrane prepared in the aforementioned step is immersed in a pre-hybridization solution containing sodium chloride at a concentration of 450 to 900 mM and sodium citrate at a concentration of 45 to 90 mM, sodium dodecyl sulfate (SDS) at a concentration of 0.1 to 1.0 wt %, denatured nonspecific DNA at a concentration of 0 to 200 μl/ml, (a preferred pre-hybridization solution contains 900 mM sodium chloride, 90 mM sodium citrate, 1.0% SDS and 100 μl/ml of modified calf-thymus DNA), and optionally albumin, Ficoll and polyvinyl pyrrolidone each at a concentration of 0 to 0.2 wt %, wherein the amount of the solution is 50 to 200 μl per 1 $cm^2$ of the membrane, and maintained at 42 to 65° C. for one to four hours.

Then the membrane is immersed in a solution obtained by mug the pre-hybridization solution as used above with the probe prepared in the aforementioned step in such an amount equivalent to $1.0 \times 10^4$ to $2.0 \times 10^6$ cpm per 1 $cm^2$ of membrane) and maintained at 42 to 65° C. for 12 to 20 hours, wherein the amount of the solution is 50 to 200 μl per 1 $cm^2$ of the membrane.

After the hybridization, the membrane is taken out and is washed at 42 to 65° C. with a washing solution containing 15 to 300 mM sodium chloride, 1.5 to 30 mM sodium citrate and 0.1 to 1.0 wt % of SDS (a preferred, washing solution contains 15 mM sodium chloride and 1.5 mM sodium citrate and 1.0% of SDS). The washed membrane is slightly rinsed with 2×SSC (300 mM sodium chloride 30 mM sodium citrate), and is then dried. This membrane is applied to the autoradiography for example, to detect the position of the probe on the membrane, whereby position of the clone of the DNA hybrid is located on the original cultivating agar medium, and the clone containing the desired DNA can be picked up and isolated. The present gene can be obtained by cultivating the clone thus obtained.

The recombinant vector according to the present invention can be obtained by cloning of the DNA prepared in the aforementioned step into the vector according to the method disclosed in "Molecular Cloning. A Laboratory Manual 2nd edition (1989)", Cold Spring Harbor Laboratory Press, "Current Protocols in Molecular Biology" (1987), John Wiley & Sons, Inc. ISBNO-471-50338-X, etc. Examples of the vector include, for example, pUC119 (Takara Shuzo Co., Ltd.), pTV118N (Takara Shuzo Co., Ltd.), pBluescriptII (Toyobo Co., Ltd.), pCR2.1-TOPO™ (Invitrogen Co., Ltd.), pTrc99A (Pharmacia) and pKK223-3 (Pharmacia) and the like.

The aforementioned DNA sequence can be analyzed by the Dideoxy method described in the Proceeding of Natural Academy of Science, by F. Sanger, S. Nicklen and A. R. Coulson, U.S.A (1977) 74: PP. 5463–5467. In order to prepare samples for analysis of the DNA sequence, it is possible to use the commercially available reagent such as ABI PRISM Dye Terminator Cycle Sequencing Ready Reaction Kit of Parkin Elmer Inc. or the like.

The activity of the enzyme protein, encoded by the obtained DNA, produced by the transformant can be confirmed by introducing a vector having a promoter in operative linkage with the obtained DNA which locates downstream of the promoter as described below to a microorganism, and allowing the cultivated product of the transformant to react with 4-bromo-3-oxobutanoate to analyze the amount of (S)-4-bromo-3-hydroxybutanoate in the reaction.

The phrase "a promoter in operative linkage with the DNA" above means that the linkage with the promoter is made in such a way that the gene of the present invention will be expressed under the control of the promoter in a host cell introduced with the gene to transform the host cell. Examples of the promoter include, for example, the lactose operon promoter of *Eschenchia coli*, tryptophan operon promoter of *Escherichia coli* and synthetic promoter such as tac promoter or trc promoter which can function in *Eschericha coli*. It is also possible to use the promoter controlling the expression of the present in *Penicillium citrinum* per se.

Generally, the present gene is introduced into the host cell in a form of a recombinat vector having a promoter in operative linkage with the DNA. A vector having a selective marker gene (e.g. antibiotic-resistance conferring gene such as kanamycin resistant gene and neomycin resistant gene), can also be used, whereby the transformant having the vector can be selected using the phenotype of the relevant selective marker gene as an indicator.

Examples of the host cell into which the vector as described above or a DNA construct having a promoter in operative linkage with the present gene can be introduced include, for example, a microorganism belonging to *Escherichia, Bacillus, Corynebacterium, Staphylococcus, Streptomyces, Sacchrmmyces, Kluyveromyces* or *Aspergillus*.

A suitable method is selected to produce the transformant in accordance with the kind of cells used as the host. Examples of such methods include the calcium chloride method disclosed in "Molecular Cloning; A Laboratory Manual 2nd edition" (1989), Cold Spring Harbor Laboratory Press, and "Current Protocols in Molecular Biology" (1987), John Wiley & Sons, Inc. ISBNO-471-50338-X, etc., and the electroporation method described in "Method in Electroporation: Gene Pulser/*E. coli* Pulser System", Bio-Rad Laboratories, (1993), etc.

The present gene contained in the transformant can be confirmed by verifying the site of the restriction enzyme, analysis of the polynucleotide sequence, Southern hybridization, Western hybridization, etc., with respect to the DNA prepared subsequent to preparation of the vector DNA from the transformant, according to the normal method given in "Molecular Cloning: A Laboratory Manual 2nd edition" (1989), Cold Spring Harbor Laboratory Press.

The present protein will be explained below.

Examples of the amino acid sequence wherein one or more amino acids are deleted, substituted or added in the amino acid sequence of SEQ ID NO: 1 include, for example, an amino acid sequence having additional 6-amino acid of Trp-Ile-Ser-Thr-Lys-Leu (SEQ ID NO: 37) at the C-terminal of the amino acid sequence of SEQ ID NO: 1 in addition to those defined in i to iii) above.

The present protein can be produced by cultivating the transformant containing the present gene.

Examples of the medium that may be used for cultivating the transfected host microorganisms include, for example, various mediums that contains a carbon source or a nitrogen source, an organic salt, an inorganic salt or the like in suitable amounts.

Examples of the carbon source include, for example, saccharides such as glucose, dextrin and sucrose, sugar alcohol such as glycerol, organic acid such as fumaric acid, citric acid and pyruvic acid, animal oil, plant oil and molasses. The amount of these carbon sources to be applied to the media is normally in the range of about 0.1 to 30% (w/v) with respect to culture solution.

Examples of the nitrogen source include, for example, a naturally occurring organic nitrogen sources such as meat extract, peptone, yeast extract, malt extract, pulverized soy bean, Corn Steep Liquor, cottonseed, dried yeast and casamino acid; ammonium salt of inorganic acid such as amino acids and sodium nitrate, ammonium salt of inorganic acid such as ammonium chloride, ammonium sulfate and ammonium phosphate; ammonium salt of organic acid such as ammonium fumarate and ammonium citrate; and urea. Of these substances, an ammonium salt of organic acid, naturally occurring nitrogen source and amino acid can also be used as carbon sources in many cases. The amount of these nitrogen sources that may be applied to the media is normally in the range of about 0.1 to 30% (w/v) with respect to culture medium.

Examples of the organic and inorganic salt include, for example, chloride, sulfate, acetate, carbonate and phosphate of calcium, sodium, magnesium, iron, manganese, cobalt and zinc. Specific examples thereof include, for example, sodium chloride, potassium chloride, magnesium sulfide, ferrous sulfide, manganese sulfide, cobalt chloride, zinc sulfate, copper sulfate, sodium acetate, calcium carbonate, monopotassium hydrogenphosphate, potassium dihydrogenphosphate and the like. The amount of these organic and/or inorganic salts that may be applied to the media is normally in the range of about 0.0001 to 5% (w/v) with respect to culture medium.

A small amount of isopropyl thio-β-D-galactoside (IPTG) can be added, as an inducer of the production of the present protein, to the medium for cultivating the transformant having a promoter (e.g. tac promoter, trc promoter and lac promoter which are induced by allolactose )in operative linkage with the gene.

Cultivation of the transformant having the present gene can be conducted by a conventional method used for cultivating a host cell such as microorganism. For example, it can be done in the following method: liquid cultivation such as test tube shake cultivation, reciprocative shaking cultivation, jar fermenter cultivation and tank cultivation, and solid cultivation.

Cultivation temperature can be varied within the range where the microorganism can grow. It is normally within the range of 15 to 40° C. Preferably, the pH value of the medium is set within the range from about 6 to 8. Cultivation time varies according to the cultivation conditions, and normally from about one to five days are preferred.

The present protein can be purified by a suitable purification method that may be usually applied to purify a protein. Examples thereof include following methods. Cells are collected by subjecting cultivated products of the transformant to centrifugation of the cultivation and collected cells are disrupted by physical disrupting such as ultrasonic treatment and French pressing, or chemical disrupting method using such a lytic enzyme as lysozyme. Impurities are removed from the obtained disrupted solution by centrifugation and membrane filter whereby cell-free extract is prepared. The extract is fractionated by a suitable separation and refining method such as cation exchange column chromatography, anion ion exchange column chromatography, hydrophobic column chromatography and gel column chromatography, whereby the present protein can be purified.

Examples of the support that may be used for the chromatography include, for example, a cellulose introduced with a carboxy methyl (CM) group, a diethyl amino ethyl (DEAE) group, a phenyl group or a butyl group, and a insoluble polymer support such as dextrin, agarose or the like. A commercially available columns charged with support can be used. Examples of the column available on the market include, for example, Q-Sepharose FF, Phenyl-Sepharose HP (trade names by Amasham Pharmacia Biotech) and TSK-gel G3000SW (trade name by Toso Co., Ltd.).

The fraction including the present protein can be selected, for example, by testing the capability of preferentially producing (S)-4-bromo-3-hydroxybutanoate by asymmetrically reducing 4-bromo-3-oxobutanoate.

Next, a description will be made to the method for producing (S)-4-halo-3-hydroxybutanoate of formula (1):

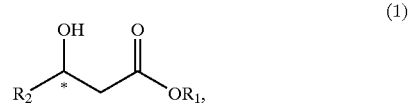

(1)

wherein $R_1$ represents an alkyl group, and $R_2$ represents a methyl group which is substituted with a halogen atom, which process comprises reacting 4-halo-3-oxobutanoate of formula (2):

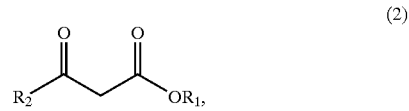

(2)

wherein $R_1$ and $R_2$ represent the same as defined above with the present enzyme, a transformant which produces the enzyme, or a treated product thereof.

In the formula (1) and (2), $R_1$ denotes C1–C8 alkyl groups, and $R_2$ denotes methyl group substituted with a halogen atom or atoms.

Examples of the C1–C8 alkyl group represented by $R_1$ include methyl, ethyl, propyl, isopropyl, butyl, isobutyl, t-butyl, pentyl, hexyl, heptyl, and octyl groups.

Examples of a methyl group which Is substituted with a halogen atom or atoms (e.g, fluorine, chroline, bromine, or iodine) represented by $R_2$ include, for example, monofluoromethyl, monochloromethyl, monobromomethyl, difluoromethyl, dichloromethyl, dibromomethyl, trifluoromethyl, and trichloromethyl groups.

Specific examples thereof include, for example, 4-halo-3-oxobutanoate ester include methyl 4-chloro-3-oxobutanoate, ethyl 4-chloro-3-oxobutanoate, propyl 4-chloro-3-oxobutanoate, methyl 4-bromo-3-oxobutanoate, ethyl 4-bromo 3-oxobutanoate, propyl 4-bromo-3-oxobutanoate, and octyl 4-bromo-3-oxobutanoate.

The production is usually carried out in the presence of water and reduced form nicotine amide adenine dinucleotide phosphate (hereinafter referred to as "NADPH"), Water used in this case may be an aqueous buffer solution, Examples of buffer agent that may be used for this aqueous buffer solution include, for example, an alkali phosphate metal salt such as sodium phosphate and potassium phosphate, alkali acetate metal salt such as sodium acetate aqueous solution and potassium acetate, and mixtures thereof The reaction may be conducted in the co-presence of an organic solvent. Examples of the organic solvent include, for example, an ether such as t-butyl methyl ether, diisopropyl ether, tetrahydrofuran or the like; an ester such as ethyl formate, ethyl acetate, propyl acetate, butyl acetate, ethyl propionate, butyl propionate or the like; a hydrocarbon such as toluene, hexane, cyclohexane, heptane, isooctane or the like; an alcohol such as methanol, ethanol, 2-propanol, butanol, t-butyl alcohol or the like; an organic sulfur compound such as dimethylsulfoxide or the like; a ketone such as acetone or the like; a nitrile such as acetonitrile or the like; and mixtures thereof.

The reacting of 4-halo-3-oxobutanoic acid ester of formula (2) with the present enzyme, a transformant which produces the enzyme, or a treated product thereof is usually conducted by stirring, shaking or mixing water, NADPH and 4-halo-3-oxobutanoate ester together with transformant or the treated substance, optionally in the presence of the organic solvent.

The pH of the reaction can be suitably set, normally within a range of 3 to 10. Reaction temperature is normally within the range of 0 to 60° C. in view of the stability of the 4-halo-3-oxobutanoate ester and a product thereof and reaction velocity.

Progress of the reaction can be monitered by, for example, tracing 4-halo-3-oxobutanoate ester in the reaction solution by means of high performance liquid chromatography or the like. The reaction time is usually in the range of 05 hour to 10 days.

After completion of the reaction, (S)-4-halo-3-hydroxybutanoate can be separated and recovered from the reaction mixture by a suitable methods. For example, the reaction mixture is subjected to post-treatment such as extraction, concentration of organic solvent, or a optional combination thereof, and the product may be further purified by column chromatography and distillation, if necessary.

The present protein, the transformant which produces the same or the treated product thereof can be used in various forms in the reaction. Examples of the applicable form thereof include, for example, the cultivated product of the transformant containing the present gene, the transformant cell containing the present gene; the treated product of thereof, cell-free extract, a crude purified protein; a purified protein; and the immobilized product thereof.

Examples of the treated product of the transformant include, for example, a freeze dried transformant, an organic solvent treated transformant, a dried transformant, a transformant ground by friction, a self-digested transformant, an ultrasonically treated transformant, an extract of the transformant and an alkali-treated transformant, Immobilized products can be obtained, for example, by the carrier bonding method (wherein the present protein is adsorbed onto an inorganic support such as silica gel, ceramic or the like, cellulose and ion exchange resin), and inclusion method (wherein the present protein is entrapped in the network structure of polymers such as polyacrylamide, a sulfur containing polysaccharide gel (e.g. carageenan gel), alginic acid gel and agar gel).

Sterilized transformants, as a treated product, is preferably used for an industrial production rather than the transformant containing the present gene per se, in view of less restriction imposed on production facilities.

Examples of the method for sterilizing the transformant for such a purpose include, for example, physical sterilization (heating, drying, freezing, light beams, ultrasound, filtration and application of electric current) and chemical sterilization (alkali, acid, halogen, oxidizing agents, sulfur, boron, arsenic, metal, alcohol, phenol, amine, sulfide, ether, aldehyde, ketone, cyan and antibiotics). Preferably selected is a method which accompanies lesser pollution or contamination in the reaction system and lesser loss of the enzymatic activity of the present protein.

The reaction is preferably conducted in the presence of NADPH. The NADPH is converted to the oxidized form if β-nicotine amide adenine dinucleotide phosphate (hereinafter referred to as "$NADP^+$") with the progress of the reaction. Since the $NADP^+$ can be converted back to the original NADPH by an enzyme capable of converting the $NADP^+$ into NADPH, such an enzyme capable of converting the $NADP^+$ into the NADPH may also be added to the reaction.

Examples of the enzyme capable of converting the $NADP^+$ into the NADPH include, for example, a glucose dehydrogenase, an alcohol dehydrogenase, an aldehyde dehydrogenase, an amino acid dehydrogenase, an organic dehydrogenase (malic acid dehydrogenase) and the like.

The activity of the glucose dehydrogenase in the reaction system can be enhanced by adding glucose thereto.

The protein capable of converting the $NADP^+$ into the NADPH can be applied or added to the reaction system in any form, for example, of the enzyme, a microorganism having the enzymatic activity or treated product thereof Alternatively, the microorganism having the activity described above may be a transformant having a gene coding for an enzyme capable of converting the $NADP^+$ into the NADPH, or a treated product of the transformant, The treated product herein includes an equivalent thereof.

The transformant having gene of the enzyme capable of converting the $NADP^+$ into the NADPH as described above and the present gene can be employed in this reaction.

Both of the genes may be introduced into a host cell by transfecting the same with a single vector having both of the genes, or with a plurality of recombinant vectors introduced with the respective gene. A further method of introducing the gene comprises introducing the present gene or both of the genes into chromosome of a host cell.

Examples of the method for introducing both of the genes into a single vector include, for example, a method for constructing a vector by linking expression control regions such as promoters and terminators to respective genes and a method of constructing a recombinat vector for expressing an operon containing multiple cistrons such as lactose operon.

Next a description will be made to the second aspect of the present invention relating to a process for producing an optically active 3-hydroxybutanoic acid ester of formula (1a) as defined above, which process comprises reacting 3-oxobutanoic acid ester of formula (2a) as defined above, with a whole cells of a microorganism or a treated product thereof, which microorganism belongs to *Penicillium citrinum, Cryptcoccus humicolus*, or *Bacillus alvei* and is capable of asymmetrically reducing the oxo group at 3-position of the compound of formula (2a) to corresponding 3-hydroxy group.

According to the second aspect of the present invention, the desired optically active ester compound can be readily produced in an industrially desirable manner.

Examples of a C1–C8 alkyl group represented by $R_1$ in the general formula (1) and (2) include methyl, ethyl, propyl, isopropyl, butyl, isobutyl, t-butyl, pentyl, hexyl, heptyl, and octyl groups.

Examples of a methyl group which may be substituted with a halogen atom or atoms represented by $R_{20}$ include methyl group and methyl groups substituted with a halogen atom or atoms. Specifically, examples of the methyl group substituted with a halogen atom or atoms include, for example, monofluoromethyl, monochloromethyl, monobromomethyl, difluoromethyl, dichloromethyl, dibromomethyl, trifluoromethyl, and trichloromethyl groups.

In the instant production method, the reaction of converting a 3-oxobutanoate of formula (1a) to an optically active 3-hydroxybutanoate of formula (2a) is achieved by employing cells or cell products of one or more microorganisms selected from the group consisting of *Penicillium citrinum, Cryptococcus humicolus*, and *Bacillus alvei*.

Specific examples of cells or cell products of microorganisms which can be used in the reaction include those of *Penicillium citrinum*, IFO 4631, *Cryptococcus humicolus* IFO 1527, and *Bacillus alvei* IFO 3343t.

The cultivation of microorganisms that can be used in this aspect of the invention can be conducted, for example, as described for the production of the transformant using the same cultivation medium and conditions in the first aspect of the present invention.

Microorganisms that may be used in the instant production method can be cultivated using media for various microorganisms comprising carbon and nitrogen sources, organic and inorganic salts, and others as appropriate.

Examples of carbon sources contained in the media include glucose, sucrose, glycerol, starch, organic acids, and molasses. Examples of nitrogen sources include yeast extract, meat extract, peptone, casamino acid, malt extract, soybean flour, corn steep liquor, cottonseed flour, dried yeast, ammonium sulfate, and sodium nitrate. Examples of organic and inorganic salts include sodium chloride, potassium chloride, sodium carbonate, monopotassium phosphate, dipotassium phosphate, calcium carbonate, ammonium acetate, manganese sulfate, copper sulfate, zinc sulfate, ferrous sulfate, and cobalt chloride.

Examples of methods for culturing include solid culture and liquid culture (such as tube culture, flask culture, and jar fermenter culture).

The temperature for cultivation and the pH of the medium are not limited to any specific values as long as they are within the range allowing the microorganisms to grow. The temperature for culturing, for example, can be in the range of 15 to 45° C. and the pH of the medium in the range of 4 to 8.

The cultivation period can be suitable set, depending on the cultivation conditions, and is usually one to seven days.

Microorganism cells obtained by cultivation can be used in the reaction according to the instant production methods without any treatment. For example, the cultivation liquid is utilized as it is, a method in which cells are harvested by centrifuging the cultivated liquid or the like, and wet cells obtained by washing the harvested cells with a buffer solution or water can be utilized.

Examples of products of microorganism cells which can be used in the present reaction include, for example, products made by subjecting cells obtained by cultivation to treatments with an organic solvent (acetone, ethanol, and the like), freeze-dried cells, alkali-treated cells, and products made by disrupting the cells physically or enzymatically. Furthermore, Examples of the cell products include those obtained by carrying out immobilization according to well-known procedures after the above-described treatments.

The reaction is usually carried out in the presence of water, and the water may be used in the form of buffer solutions. Examples of buffering agents that may be used in the buffer solutions include, for example, alkali metal salts of phosphoric acid such as sodium phosphates and potassium phosphates, and alkali metal salts of acetic acid such as sodium acetate and potassium acetate. In such cases, the pH of the aqueous layer during the reaction can be varied, if necessary, in the range where the reaction proceeds, and is usually in the range of 3 to 10.

The reaction can further utilize a hydrophobic organic solvent, such that the reaction can be carried out in the bilayer system of water and such a hydrophobic organic solvent. Examples of hydrophobic organic solvents that may be used in this case include, for example, an ester such as ethyl formate, ethyl acetate, propyl acetate, butyl acetate, ethyl propionate, butyl propionate or the like, an alcohol such as n-butyl alcohol, n-amyl alcohol, n-octyl alcohol or the like; an aromatic hydrocarbon such as benzene, toluene, xylene or the like, an ether such as diethyl ether, diisopropyl ether, methyl-t-butyl ether or the like, a halogenated hydrocarbon such as chloroform, 1,2-dichloroethane or the like, and a mixture thereof.

The concentration of the starting compound in the reaction, the 3-oxobutanoate of formula (1a), is usually 50% (w/v) or less. In order that the concentration of the 3-oxobutanoate of formula (1a) in the reaction system be maintained at an almost constant level, the 3-oxobutanoate of formula (1a) may be added to the reaction system in a continuous or successive manner.

The reaction temperature is usually in the range of 0 to 60° C.

In the reaction, saccharides such as glucose, sucrose, and fructose, alcohols such as ethanol, surfactants can optionally be added.

The reaction time is usually in the range of 0.5 hour to 10 days. The progress of the reaction can be monitored, for example, by determining the amount of the starting compound in the reaction solution with high performance liquid chromatography, gas chromatography, or the like, after the addition of a 3-oxobutanoate of formula (1a).

After completion of the reaction, an optically active 3-hydroxybutanoate of formula (2a) can be isolated by subjecting the reaction solution to usual post-treatments such as extraction with an organic solvent, concentration, etc. The isolated compound can be further purified with column chromatography, distillation, or the like, if necessary.

Next a description will be made to the third aspect of the present invention relating to a process for producing an optically active 4-bromo-3-hydroxybutanoate of formula (1b) as defined above, which process comprises reacting 4-bromo-3-oxobutanoate of formula (2b) as defined above with an enzyme having an amino acid sequence as defined in iv) to vi) above, which enzyme will be referred to as "the instant enzyme".

Examples of the C2–C8 alkyl group represented by $R_1$ in the 4-bromo-3-oxobutanoate of formula (1a) include, for example, ethyl, propyl, isopropyl, butyl, pentyl, hexyl and octyl groups.

The polynucleotide sequence coding for an enzyme having the amino acid sequence shown in SEQ ID NO: 34 which can be employed in the instant production method is shown in SEQ ID NO: 35 (Appl. Microbiol. Biotechnol. (1999) 52, 386–392). The present polynucleotide may be naturally occurring or produced by a suitable mutation of the naturally occurring sequence such as point mutations, mutagenic treatments, or the like.

pUAR containing the DNA shown in SEQ ID NO: 35 is deposited undr the Butapest Treaty with the Deposition No.

FERM BP-7752, which had been originally deposited under FERM P-18127 with an International Patent Organism Depositary, National Institute of Advanced Industrial Science and Technology.

The instant enzyme can be produced, for example, by cultivating microorganisms containing the instant polynucleotide of SEQ ID NO: 34.

The microorganism containing the instant polynucleotide of SEQ ID NO: 35 can be obtained by cultivating a transformed microorganism host cell transfected with a vector having the polynucleotide of SEQ ID NO: 35.

Examples of host cells include, for example, microorganisms belonging to *Eschericha, Bacillus, Corynebacterium, Staphylococcus, Streptomyces, Saccharomyces, Kluyveromyces*, and *Aspergillus*.

Introduction of the polynucleotide into the host cell can be accomplished by a suitable conventional method, depending on the kind of cells used as the host. Examples of the methods include calcium chloride methods described in "Molecular Cloning; A Laboratory Manual, 2nd edition" (1989), Cold Spring Harbor Laboratory Press, "Current Protocols in Molecular Biology" (1987), John Wiley & Sons, Inc., ISBNO-471-50388-X, etc., and electroporation methods described in "Methods in Electroporation: Gene Pulser/*E. coli* Pulser System", Bio-Rad Laboratories, (1993), etc.

Transformed microorganisms having the desired polynucleotide can be selected using, as an index, the phenotype or the like of a selectable marker gene contained in a vector, which include those described above in the first aspect of the present invention, It can be confirmed as to whether the transformed microorganisms carry the gene by preparing the vector DNA from the transformed microorganisms, and then subjecting the prepared vector DNA, for example, to a usual method (identification of restriction enzyme sites, analysis of the polynucleotide sequence, southern hybridization, or the like) as described in "Molecular Cloning" (J. Sambrook et al., Cold Spring Harbor, 1989) and others.

Cultivation of the transformed cells to express the desired enzyme can be conducted by using, as a medium for culturing the above-described microorganisms, various kinds of medium including those comprising carbon and nitrogen sources commonly used in culturing microorganisms, and organic and inorganic salts, and others as appropriate.

Examples of carbon sources include: saccharides such as glucose, dextrin and sucrose; sugar alcohols such as glycerol; organic acids such as fumaric, citric and pyruvic acids; animal and vegetable oils; and molasses, The amount of these carbon sources to be added into the medium may be usually in the range of 0.1 to 20% (w/v) with respect to the entire medium volume.

Examples of nitrogen sources are organic or inorganic nitrogen sources, including: natural organic nitrogen sources or amino acids such as meat extract, peptone, yeast extract, malt extract, soybean flour, corn steep liquor, cottonseed flour, dried yeast and casamino acid; inorganic acid ammonium salts and nitrates such as sodium nitrate, ammonium chloride, ammonium sulfate and ammonium phosphate; organic acid ammonium salts such as ammonium fumarate and ammonium citrate; and urea. Among these, organic acid ammonia salts, natural organic nitrogen sources, amino acids, and the like can also be used as carbon sources in many cases. The amount of nitrogen sources to be added may be usually in the range of 0.1 to 30% (w/v) with respect to the entire medium volume.

Examples of organic and inorganic salts may include chlorides, sulfates, acetates, carbonates and phosphates of potassium, sodium, magnesium, iron, manganese, cobalt, zinc, and others. Specifically, examples of such salts include sodium chloride, potassium chloride, magnesium sulfate, ferrous sulfate, manganese sulfate, cobalt chloride, zinc sulfate, copper sulfate, sodium acetate, calcium carbonate, sodium carbonate, monobasic potassium phosphate, dibasic potassium phosphate, and others. The amount of an organic or inorganic salt to be added may se usually in the range of 0.0001 to 5% (w/v) with respect to the entire medium volume.

A small amount of isopropyl thio-$\beta$-D-galactoside (IPTG) can be added, as an inducer of the production of the instant protein, to the medium for cultivating the transformant having a promoter (e.g. tac promoter, trc promoter and lac promoter which are induced by allolactose )in operable linkage with the gene of the instant protein.

Cultivation can be carried out according to procedures commonly used for cultivating microorganisms. Examples of the procedures include, for example, liquid culture such as tube-shaking culture, reciprocally shaking culture, jar fermenter culture, and tank culture; and solid culture. When a jar fermenter is used, it is necessary to introduce sterile air into the jar fermenter, and an aeration rate of about 0.1 to about 2 times the volume of the cultivating medium per minute is usually chosen. The temperature for cultivation can be varied within the range where microorganisms stay viable, and usually, cultivation temperatures in the range of about 15° C. to about 40° C. are preferred. The pH of the medium is preferably in the range of about 6 to about 8. The period for culturing is varied depending on culturing conditions, and a period from about one day to about five days is desirable in usual cases.

Cells containing the instant enzyme thus produced, cell products, or purified materials of the instant enzyme can be used in this aspect of the invention.

Examples of cell products include, for example, freeze-dried cells, organic solvent treated cells, dried cells, triturated cells, cell autolysates, sonicated cells, cell extracts, alkali-treated cells, and in addition, products obtained by immobilizing these by commonly employed methods.

Purified enzyme can be produced, for example, by purifying the instant enzyme from cultures of microorganisms carrying the instant enzyme.

The instant enzyme isolated from cultures of the microorganisms, may be further purified a conventional method as used for the purification of ordinary proteins.

For example, cells are harvested from the cultivated microorganism by centrifugation or the like, and these cells are homogenized by physical disrupting procedures such as an ultrasonic treatment, Dynomill treatment and French press treatment, or by chemical disrupting procedures using surfactants or cell-lytic enzymes such as lysozyme. Insoluble materials are usually removed from the resultant homogenate by centrifugation, membrane filtration, or the like to prepare a cell-free extract, which will be then fractionated through separation and purification procedures such as cation exchange column chromatography, anion exchange column chromatography, hydrophobic column chromatography, gel column chromatography, and the like to purify the instant enzyme. Examples of the support that may be used for the chromatography include, for example, resin support such as cellulose, dextran and agarose, having an carboxymethyl (CM), DEAE, phenyl, butyl group, or the like. Commercially available carrier-packed columns may also be used, such as Q-Sepharose FF, Phenyl-Sepharose HP (trade name, both manufactured by Amersham Pharmacia Biotech), TSK-gel G3000SW (trade names manufactured by Toso Co., Ltd.), and others.

Next, the instant production method will be described.

4-bromo-3-oxobutanoate of formula (1b) is converted to an optically active 4-bromo-3-hydroxybutanoate of formula (2b) by subjecting a 4-bromoacetoacetic acid ester compound of formula (1b) to the reaction with the instant enzyme.

The reaction is usually carried out in the presence of water, and the water can be in the form of buffer solutions. Examples of buffering agents that may be used include, for example, alkali metal phosphates such as sodium phosphates and potassium phosphates; alkali metal salts of acetic acid such as sodium acetate and potassium acetate.

The pH in this case can be varied within the range where the reaction proceeds. The pH is usually optionally set within the range of pH 4 to 10.

The amount of the buffer that may be used is usually 100 parts by weight or less per one part by weight of a 4-bromo-3-oxobutanoate of formula (1b).

The reaction temperature for the above-described reaction is between 0 and 70° C. in view of stability and reaction rate of the instant enzyme, and preferably between 10 and 40° C.

The reaction can also be carried out in the co-presence of an organic solvent. Examples of the organic solvent include, for example, an ether such as tetrahydrofuran t-butyl methyl ether, isopropyl ether or the like, a hydrocarbon such as toluene, hexane, cyclohexane, heptane, isooctane, decane or the like, an alcohol such as t-butanol, methanol, ethanol, isopropanol, n-butanol or the like, a sulfoxide such as dimethylsulfoxide or the like; a ketone such as acetone or the like; a nitrile such as acetonitrile or the like, and a mixture thereof.

The amount of an organic solvent that may be used in the reaction is usually 100 parts by weight or less, and preferably 50 parts by weight or less, per one part by weight of 4-bromoacetoate of formula (1b).

A coenzyme (e.g., NADH, NADPH) may also be added for the above-described reaction. The amount of the coenzyme that may be used in the reaction is usually 0.5 part or less, and preferably 0.1 part or less, per one part by weight of 4-bromo-3-oxobutanoate of formula (1b), by weight.

Additional substances described below is preferably added together with the coenzyme in order to enhance the coenzyme efficiency:

1) compound(s) such as formic acid, glucose, isopropanol, 2-butanol, 2-pentanol, 2-hexanol, 2-heptanol, 2-octanol, and the like, wherein the amount of these compounds the may be used is 100 parts or less by weight, and preferably 10 parts or less by weight, per one part by weight of 4-bromo-3-oxobutanoate of formula (1b); and 2) dehydrogenase such as formate dehydrogenase, glucose dehydrogenase, and the like, wherein the amount of dehydrogenase to be used is 0.1 part or less by weight, and preferably 0.05 part or less by weight, per one part by weight of 4-bromo-3-oxobutanoate of formula (1b).

The reaction can be carried out, for example, by stirring and shaking a mixture of water, a 4-bromo-3-oxobutanoate of formula (1b), the instant enzyme, a coenzyme, if necessary, an organic solvent, and others.

The progress of the reaction can be monitored, for example, by checking the amount of the starting compound in the reaction solution with high performance liquid chromatography, gas chromatography, or the like. The range of the reaction time is usually a period varying from five minutes to four days.

After completion of the reaction, for example, the reaction solution can be extracted with an organic solvent such as hexane, heptane, tert-butyl methyl ether, ethyl acetate, toluene, or the like) and the organic layer can be dried and concentrated, thereby obtaining the desired product. The product can be further purified by column chromatography or the like, if necessary.

The instant production method can also be performed, for example, by using a polynucleotide constructed by subjecting the polynucleotide of SEQ ID NO: 35, for example, to well-known techniques for causing a point mutation or mutations in the polynucleotide such as the site-specific mutation, a recombinant method by cleaving the polynucleotide selectively or deleting, substituting or adding a suitably selected nucleotide or nucleotides, and ligating the resulting polynucleotide sequences to obtain a desirably modified polynucleotide, or an oligonucleotide mutation method, thereby producing a polynucleotide that codes for an enzyme capable of reducing a 4-bromo-3-oxobutanoate of formula (1b) to an optically active 4-bromo-3-hydroxybutanoate of formula (2b); and carrying out the preparation of transformants, cultivation and reaction in the above described method.

Next a description will be made to the fourth aspect of the present invention relating to a process for producing 4-cyano-3-hydroxybutanoic acid, which comprises reacting 4-bromo-3-hydroxybtanoic acid ester with a metal cyanide in the presence of an alkaline earth metal hydroxide and an alkaline earth metal halogenide.

According to this aspect of the present invention, 4-cyano-3-hydroxybutanoic acid or ester thereof can be obtained in a good yield.

A racemic or optically active 4-bromo-3-hydroxybutanoic acid ester can be used in this process. Examples of the ester include, for example, a lower alkyl ester of 4-bromo-3-hydroxybutanoic acid and optically active isomer thereof. Specific examples of the lower alkyl ester include, for example, C1–C5 alkyl esters such as a methyl, ethyl, propyl, isopropyl, or butyl ester.

Examples of the metal cyanide to be used include, for example, sodium cyanide and potassium cyanide.

Examples of the alkaline earth metal hydroxide used include, for example, magnesium hydroxide, calcium hydroxide, and barium hydroxide.

Examples of the alkaline earth metal halide used include, for example, alkaline earth metal chloride and alkaline earth metal bromide, and preferred is calcium chloride.

The reaction of the 4-bromo-3-hydroxybutanoic ester and metal cyanide in the presence of an alkaline earth metal hydroxide and an alkaline earth metal halide is prefereably carried out in the presence of water An organic solvent can also be added, if necessary.

The reaction temperature is normally from −10 to 100° C., or preferably, from −10 to 40° C.

An amount of the metal cyanide that may be used in the reaction is normally from 0.8 to 2 moles per mol of 4-bromo-3-hydroxybutanoic acid ester.

An amount of the alkaline earth metal hydroxide and alkaline earth metal halide to be used in the reaction is preferably from 0.8 to 5 moles per mol of 4-bromo-3-hydroxybutanoic acid ester.

The progress of the reaction can be monitored by checking the amount of 4-bromo-3-hydroxybutanoic acid using such an analysis means as the gas chromatography, the high-performance liquid chromatography, the thin layer chromatography or the like.

After completion of the reaction, for example, an inorganic acid such as hydrochloric acid is usually added to the reaction solution, thereafter the resulting mixture may be extracted with an organic solvent and the obtained organic layer is typically concentrated to obtain the 4-cyano-3-hydroxybutanoic acid.

The 4-Bromo-3-hydroxybutanoic ester and metal cyanide are made to react in the presence of an alkaline earth metal hydroxide and an alkaline earth metal halide, and the resulting mixture is then allowed to react with dialkyl sulfuric acid to produce the 4-cyano-3-hydroxybutanoic acid ester.

The reaction of the 4-cyano-3-hydroxybutanoic acid obtained as above with a dialkyl sulfuric acid is usually carried out in the presence of a base, preferably in a solvent.

Examples of the solvent that may be used in the reaction include, for example, an ester such as ethyl acetate, butyl acetate or the like, an ether such as tetrahydrofuran, 1,4-dioxyane or the like, water and a mixture thereof. Examples of the base include, for example, tertiary amines such as pyridine, 4-dimethylamino pyridine, triethylamine and diisopropylethylamine.

The reaction is conducted normally from 0 to 100° C.

The dialkyl sulfuric acid is usually used in an amount of from 1 to 2 moles and the base is usually used in an amount of from 1 to 3 moles per mol of the 4-cyano-3-hydroxybutanoic acid.

The progress of the reaction can be monitored by checking the amount of the 4-bromo-3-hydroxybutanoic acid using analytical means such as gas chromatography, the high-performance liquid chromatography, thin layer chromatography or the like.

After completion of the reaction, for example, saturated sodium bicarbonate solution is added to the reaction mixture, thereafter, the mixture is usually extracted with an organic solvent and the obtained organic layer is concentrated to give the 4-cyano-3-hydroxybutanoic acid ester.

The reaction of the dialkyl sulfate with the resulting 4-cyano-3-hydroxybutanoic acid is usually carried out after isolating the acid or the reaction can be conducted by reacting the dialkyl sulfate with the reaction mixture containing 4-cyano-3-hydroxybutanoic acid produced, wherein dialkyl sulfuric acid is preferably added to the reaction mixture.

The following describes the present invention in detail with reference to embodiments, which by no means limit the scope of the present invention.

REFERENCE EXAMPLE 1

100 ml of medium (potato dextrose broth (by Vecton Dickinson) dissolved to water at a ratio of 24 g/L) was put into a 500 ml flask, and was sterilized at 121° C. for 15 minutes. Then 0.5 ml of one strain of *Penicillium citrinum* IF04631 cultivated in the medium of the same composition (cultured by shaking at 30° C. for 48 hours) was added to it, and was shaken and cultured at 30° C. for 72 hours. Then the obtained cultivation solution was centrifuged (8000×g for ten minutes), and the resulted precipitation was collected. This precipitation was washed in 50 ml of 20 mM potassium phosphate buffer (pH7) three times to obtain about 1.0 g of wet bacterial cell.

10 g of said wet bacterial cell was used to prepare total RNA according to the guanidine phenol chloroform thiocyanate method, and about 1.5 mg of total RNA was obtained Further, about 9.3 µg of RNA containing poly(A) was obtained from 0.5 mg of total RNA using oligotex(dT)30-Super (Takara Shuzo Co., Ltd.).

cDNA library was prepared according to the Gubler and Hoffman method as follows. A single-stranded cDNA was prepared using the RNA (3.0 µg) containing the above poly (A), Oligo(dT) 18-linker primer ((including XhoI site) Takara Shuzo Co., Ltd.) and RAV-2 Rtase and SuperScriptII Rtase. *E. Coli* DNA polymerase, *E.coli* Rnase/*E. coli* DNA ligase mixture and T4 DNA polymerase was added to this reaction solution to carry out double stranded cDNA synthesis and smooth terminalization. This was followed by ligation between this double stranded cDNA and EcoRI-NotI-BamHI adaptor (Takara Shuzo Co., Ltd.). The DNA was ligated, phosphorylated and was digested by XhoI. The low molecular weight DNA was removed by the spin column (Takara Shuzo Co., Ltd.), and λ ZapII (EcoRI-XhoII digest) and ligation were performed. After that, packaging was made using the in vitro packaging kit (Stratagene Inc.), whereby a cDNA library (hereinafter referred to as "cDNA library" (A)) was obtained.

EXAMPLE 1

(1) 23 g of wet bacterial cells of the *Penicillium citrinum* IF04631 strain which were prepared under the same conditions as those of the Reference Example 1 were suspended in 50 mM potassium phosphate buffer (pH 7.0) and were disrupted by Dynomill (manufactured by Symal Enterprise Inc., a glass bead 0,1 to 0.2 mm in diameter, at 3000 rpm for 30 minutes). The disrupted solution obtained in this step was subjected to centrifugal separation (10,000×g for 10 minutes). The supernatant was further subjected to ultracentrifugation (100,000×g for 120 minutes) to give 160 ml of untracentrifuged supernatant.

Ammonium sulfate was gradually added to 160 ml of the ultracentrifuged supernatant obtained in the aforementioned step until the concentration reached 1.5M. Then the solution is spread over hydrophobic interaction chromatography column [Hi-LoadPhenyl (26/10) (manufactured by Amasham Pharmacia Biotech), which was equibrated with BIS-TRIS-PROPANE buffer (20 mM, pH 7.0) containing 1.5M ammonium sulfate], and eluted, as a mobile phase, with a BIS-TRIS-PROPANE buffer (concentration gradient of ammonium sulfate: 1.5M→0.6M) containing ammonium sulfate. Thus, 20 ml of eluted fraction with an ammonium sulfate concentration of 1.1 to 0.9M was obtained as a fraction having a reducing enzyme activity.

The eluted fraction was subjected to desalination and was replaced by Tris-HCl buffer solution (20 mM, pH 7.7), and then spread over the ion exchange chromatography column [Hi-Load Q Sepharose (16/10) (manufactured by Amasham Pharmacia Biotech), which is buffered by Tris-HCl buffer solution (20 mM, pH7.7)]. Tris-HCl buffer solution (concentration gradient of sodium chloride: 0→0.5M) containing sodium chloride was used as a mobile phase to elute. Thus, 3 ml of a fraction containing a sodium chloride at a concentration of 0.02 to 0.08M was obtained as a fraction having reducing enzyme activity. The fraction was concentrated and the concentrated solution was subjected to gel filtration (column: Superdex 200 (10/30) (manufactured by Amasham Pharmacia Biotech)) [mobile phase: BIS-TRIS-PROPANE buffer (20 mM, pH7.0)]. Thus, 1 ml of a fraction corresponding to a molecular weight of about 33000 Dalton (hereinafter referred to as "active fraction (A)") was obtained as a fraction having a reducing enzyme activity.

The reducing enzyme activity of the fraction obtained by chromatography or the like was measured according to the following steps.

The eluted fraction obtained by the chromatography was added to 0.9 ml of phosphoric acid buffer solution (20 mM, pH7.0) containing methyl 4-bromo-3-oxobutanoate (1.56 mg/ml) and NADPH (0.226 mg/ml) to make a total volume of 1 ml. After it was maintained at 37° C. for 20 seconds, the absorbance of 340 nm was measured. The NADPH consumption was calculated from the absorbance of 340 nm, thereby recovering the reducing enzyme activity of the fraction.

(2) The active fraction (A) obtained in the aforementioned step was subjected to SDS polyacryl amide gel electrophoresis according to the method described in "Laemmli, U. K., Nature, (1970) 227, 680". The gel after the electrophoresis was stained with a stain solution, Coomassie brilliant blue G250 (manufactured by Bio-Rad Inc.), and the gel on the stained portion was cut off. This gel was subjected to reductive alkylation by dithiothreitol and acetoamide iodide. After trypsin-treatment, a peptide was extracted from the gel. The extracted peptide was fractionated by HPLC (column: TSK gel ODS-80=Ts, 2.0 mm×250 mm (Toso Co., Ltd.), mobile phase: concentration gradient of 0.1% aqueous trifluoroacetate/acetonitrile=100/0→20/80). A protein sequencer (494cLC) was used to determine the amino acid sequences using the five fractions, which were found to be highly pure according to the TOS-MS. The amino acid sequences determined are shown in SEQ ID NOs: 3, 4, 5, 6 and 7.

(3) The oligonucleotide primers of SEQ ID NOs: 8, 9, 10, 11, 12, 13 and 14 was synthesized based on the amino acid sequence of SEQ ID NO: 3.

PCR was conducted by using any one of the oligonucleotide primers of SEQ ID NOs. 8, 9, 10, 11, 12, 13 and 14, and a SK oligonucleotide primer (by Stratagene) as a primer, and the aforementioned cDNA (A) as a template in the reaction solution having the following composition under the following reaction conditions. (Expand High Fidelity PCR System manufactured by Rosche Diagnostic was used.)

Composition of Reaction Solution:

| cDNA library stock solution | 1 µl |
| dNTP (each 2.5 mM-mix) | 0.4 µl |
| Primer (20 pmol/µl) | 0.75 µl each |
| 10 × buffer (with MgCl) | 5 µl |
| enz. expandHiFi (3.5 × 10³ U/ml) | 0.375 µl |
| Deionized water | 41.725 µl |

Reaction Conditions:

The reaction vessel containing the reaction solution of the aforementioned composition was set to the PERKIN ELMER-GeneAmp PCR System 2400, and was heated at 97° C. (for 2 minutes). Then a cycle of 97° C. (0.25 min.)→50° C. (0.5 min.)→72° C. (1.5 min.) was repeated ten times, followed by a cycle of 97° C. (0.25 min.)→55° C. (0.5 min.)→72° C. (2.5 min.) repeated twenty times, and maintained at 72° C. (7 min.).

Thereafter, a portion of the PCR reaction solution was subjected to agarose gel electrophoresis, and a band of a DNA fragment of about 740 bp was detected for the following cases: the oligonucleotide primer containing the polynucleotide sequence of SEQ ID NO: 10 and the SK oligonucleotide primer were used as a primer; the oligonucleotide primer containing the polynucleotide sequence of SEQ ID NO: 12 and the SK oligonucleotide primer were used as a primer; and the oligonucleotide primer containing the polynucleotide sequence of SEQ ID NO: 14 and the SK oligonucleotide primer were used as a primer.

Using each of the PCR reaction solutions where the band of a DNA fragment of about 740 bp was detected, each of the aforementioned DNA fragments of about 740 bp was ligated to the existing "PCR product insertion site" of the p CR2.1-TOPO vector (where TOPO™ TA cloning kit manufactured by Invitrogen was used). E. coli DH5 α was transformed with the obtained ligation solution. 30 µl of 4% aqueous solution of 5-bromo-4-chloro-3-indolyl-β-D-galactocide (hereinafter referred to as "X-gal") and 30 µl of 0.1M IPTG were applied onto the LB (1% bactotrypton, 0.5% bacto yeast-extract and 1% sodium chloride) agar medium containing 50 µg/ml of ampicillin. The transformant obtained was inoculated onto it, and was incubated. Of the colonies formed, each of the white ones was picked up and was inoculated into a sterilized LB medium (2 ml) containing 50 µg/ml of ampicillin. It was incubated in a test tube under shaking (at 30° C. for 24 hours). Plasmid was prepared from each cultivated bacterial cells using the QIAprep Spin Miniprep Kit (manufactured by Qiagen).

Hereinafter, the plasmid derived from the DNA fragment obtained by PCR using the oligonucleotide primer of SEQ ID NO: 10 and SK oligonucleotide primer as a primer, will be described as "p27-1"; the plasmid derived from the DNA fragment obtained by PCR using the oligonucleotide primer of SEQ ID NO: 12 and SK oligonucleotide primer as a primer, will be described as "p27-2"; and the plasmid derived from the DNA fragment obtained by PCR using the oligonucleotide primer of SEQ ID NO: 14 and SK oligonucleotide primer will be described as "p27-3";

The polynucleotide sequence of the DNA fragment inserted into each of plasmids p27-1, p27-2 and p27-3 was analyzed, and it was found that the polynucleotide sequences of the inserted DNA fragments were identical except for the primer sequence portions.

The polynucleotide sequence of the DNA fragment inserted into plasmid p27-1 is shown in SEQ ID NO: 15.

Analysis of the polynucleotide sequence of the DNA fragment inserted into the plasmid was made as follows: Sequence reaction was carried out according to the Dye Terminator Cycle Sequence FS Ready Reaction Kit (by Perkin Elmer) with each plasmid used as a template, and the polynucleotide sequence of the obtained DNA was analyzed by the DNA sequencer 373A (by Perkin Elmer).

(4) Oligonucleotide primers containing the polynucleotide sequence of SEQ ID NO. 16 or 17 was synthesized based on the polynucleotide sequence of SEQ ID NO: 15.

PCR was conducted by using the reaction solution of the following composition and reaction conditions, wherein the oligonucleotide primers containing of SEQ ID NO: 16 and SK oligonucleotide primers (by Stratagene), or the oligonucleotide primer of SEQ ID NO: 17 and T7 oligonucleotide primer (by Stratagene) were used as a primer, and the aforementioned cDNA (A) was employed as a template. (Expand High Fidelity PCR System by Rosche Diagnostic was used.)

Composition of Reaction Solution:

| cDNA library stock solution | 1 µl |
| dNTP (each 2.5 mM-mix) | 0.4 µl |
| Primer (20 pmol/µl) | 0.75 µl each |
| 10 × buffer (with MgCl) | 5 µl |
| enz. expandHiFi (3.5 × 10³ U/ml) | 0.375 µl |
| Deionized water | 41.725 µl |

Reaction Conditions:

The reaction vessel containing reaction solution of the aforementioned composition was set to the PERKIN ELMER-GeneAmp PCR System 2400, and was heated at 97° C. (for 2 minutes). Then a cycle of 97° C. (0.25 min.)→55° C. (0.5 min.)→72° C. (1.5 min.) was repeated ten times, followed by twenty times a cycle of 97° C. (0.25 min.)→55° C. (0.5 min.)→72° C. (2.5 min.). Further, it was maintained at 72° C. for 7 minutes.

Thereafter, a portion of the PCR reaction solution was subjected to agarose gel electrophoresis. A band of DNA fragment of about 350 bp was detected when the oligonucleotide primer containing the polynucleotide sequence of SEQ ID NO: 16 and the SK oligonucleotide primer were used as a primer. A band of a DNA fragment of about 650 bp was detected when the oligonucleotide primer containing the polynucleotide sequence of SEQ ID NO: 17 and T7 oligonucleotide primer were used as a primer.

Using the PCR reaction solution containing the DNA fragment of about 350 bp obtained in the aforementioned PCR or the PCR reaction solution containing the DNA fragment of about 650 bp, the aforementioned DNA fragment of about 350 bp and the DNA fragment of about 650 bp were ligated respectively to the existing "PCR product insertion site" of the p CR2.1-TOPO vector (where TOPO™ TA cloning kit by Invitrogen was used). *E. coli* DH5 α was transformed with the obtained ligation solution. 30 μl of 4% aqueous solution of X-gal and 30 μl of 0.1M IPTG were applied to the LB agar medium containing 50 μg/ml of ampicillin. The transformant obtained was inoculated thereon, and was incubated. Of the colonies formed, each of the white ones was picked up and was inoculated into a sterilized LB medium (2 ml) containing 50 μg/ml of ampicillin. It was incubated under shaking in a test tube (at 30° C. for 24 hours). Plasmid was prepared from each cultivated bacterial cells using the QIAprep Spin Miniprep Kit (by Qiagen).

Hereinafter, the plasmid derived from the DNA fragment obtained by PCR using the oligonucleotide primer of SEQ ID NO: 16 and SK oligonucleotide primer as a primer, will be denoted by plasmid pBR-1; and the plasmid derived from the DNA fragment obtained by PCR using the oligonucleotide primer of SEQ ID NO: 17 and T7 oligonucleotide primer as primers, will be denoted by pBR-2.

The polynucleotide sequence of the DNA fragment inserted into each of plasmids pBR-1 and pBR-2 was analyzed. The polynucleotide sequence of the DNA fragment inserted into plasmid pBR-1 is shown in SEQ ID NO: 18. The polynucleotide sequence of the DNA fragment inserted into plasmid pBR-2 is shown in SEQ ID NO: 19.

Analysis of the polynucleotide sequence of the DNA fragment inserted into the plasmid was made as follows: Sequence reaction was carried out according to the Dye Terminator Cycle Sequence FS Ready Reaction Kit (by Perkin Elmer) with each plasmid used as a template, and the polynucleotide sequence of the obtained DNA was analyzed by the DNA sequencer 373A (by Perkin Elmer).

(5) And oligonucleotide primer of SEQ ID NO: 20 was synthesized based on the polynucleotide sequence of SEQ ID NO: 15. An oligonucleotide primer of SEQ ID NO: 21 was synthesized based on the polynucleotide sequence of SEQ ID NO: 19.

PCR was conducted using the following composition of reaction solution and reaction conditions, wherein the oligonucleotide primer of SEQ ID No: 20 and the oligonucleotide primer of SEQ ID NO: 21 were used as a primer, and the aforementioned cDNA library (A) was employed as a template. (Expand High Fidelity PCR System by Rosche Diagnostic was used.)

Composition of Reaction Solution:

| | |
|---|---|
| cDNA library stock solution | 1 μl |
| dNTP (each 2.5 mM-mix) | 0.4 μl |
| Primer (20 pmol/μl) | 0.75 μl each |
| 10 × buffer (with MgCl) | 5 μl |
| enz. expandHiFi (3.5 × 10³ U/ml) | 0.375 μl |
| Deionized water | 41.725 μl |

Reaction Conditions:

The reaction vessel containing reaction solution of the aforementioned composition was set to the PERKIN ELMER-GeneAmp PCR System 2400, and was heated at 97° C. (for 2 minutes). Then a cycle of 97° C. (0.25 min.)→55° C. (0.5 min.)→72° C. (1.5 min.) was repeated ten times, followed by twenty times a cycle of 97° C. (0.25 min.)→55° C. (0.5 min.)→72° C. (2.5 min.). Further, it was maintained at 72° C. for 7 minutes.

Thereafter, a portion of the PCR reaction solution was subjected to agarose gel electrophoresis. A band of a DNA fragment of about 400 bp was detected.

Using the PCR reaction solutions containing the DNA fragment of about 400 bp obtained in the aforementioned PCR was ligated to the existing "PCR product insertion site" of the pCR2.1-TOPO vector (TOPO™ TA cloning kit by Invitrogen was used). The obtained ligation solution was utilized to transform *E. coli* DH5 α.

30 μl of 4% aqueous solution of X-gal and 30 μl of 0.1M IPTG were applied to the LB agar medium containing 50 μg/ml of ampicillin. The transformant obtained was inoculated thereto, and was incubated. Of the colonies formed, each of the white ones was picked up and was inoculated into a sterilized LB medium (2 ml) containing 50 μg/ml of ampicillin. It was incubated under shaking in a test tube (at 30° C. for 24 hours). Plasmid was prepared by using the QIAprep Spin Miniprep Kit (by Qiagen) from each cultivated bacterial cells. (Hereinafter, this will be described as plasmid plasmid pBR-3).

The polynucleotide sequence of the DNA fragment inserted into each of plasmid pBR-3 was analyzed. The polynucleotide sequence of the DNA fragment inserted into plasmid pBR-3 is shown in SEQ ID NO: 22.

Analysis of the polynucleotide sequence of the DNA fragment inserted into the plasmid was made as follows: Sequence reaction was carried out by using the Dye Terminator Cycle Sequence FS Ready Reaction Kit (by Perkin Elmer) and plasmid pBR-3 as a template, and the polynucleotide sequence of the obtained DNA was analyzed by the DNA sequencer 373A (by Perkin Elmer).

ORF search was conducted based on the SEQ ID NOs. 18, 19 and 22 to determine the polynucleotide sequence (SEQ ID NO: 28) of the gene coding for the protein capable of preferentially producing methyl (S)-4-bromo-3-hydroxybutanoate by asymmetrically reducing methyl 4-bromo-3-oxobutanoate contained in the *Penicillium citrinum* IFO4631 strain. Further, amino acid sequence of SEQ ID NO: 1 of the protein was determined based on the polynucleotide sequence of SEQ ID NO: 28. Comparison between SEQ ID NO: 1 and SEQ ID NOs. 3, 4, 5, 6, and 7 showed that the amino acid sequence of SEQ ID NOs. 3, 4, 5, 6, and 7 almost coincide with a part of the amino acid sequence of SEQ NO: 1.

EXAMPLE 2

(1) The oligonucleotide primer of SEQ ID NO: 28 was synthesized based on the polynucleotide sequence of SEQ ID NO: 18, and that of SEQ ID NO: 24 was synthesized based on the polynucleotide sequence of SEQ ID NO: 19.

PCR was conducted according to the following composition of reaction solution and reaction conditions, wherein the oligonucleotide primers containing the polynucleotide sequences of SEQ ID NOs. 23 and 24 were used as primers, and the aforementioned cDNA (A) was employed as a template. (Expand High Fidelity PCR System by Rosche Diagnostic was used.)

Composition of Reaction Solution:

| cDNA library stock solution | 1 µl |
| dNTP (each 2.5 mM-mix) | 0.4 µl |
| Primer (20 pmol/µl) | 0.75 µl each |
| 10 × buffer (with MgCl) | 5 µl |
| enz. expandHiFi (3.5 × 10³ U/ml) | 0.375 µl |
| Deionized water | 41.725 µl |

Reaction Conditions:

The vessel containing reaction solution of the aforementioned composition was set to the PERKIN ELMER-GeneAmp PCR System 2400, and was heated at 97° C. (for 2 minutes). Then the cycle of 97° C. (0.25 min.)→55° C. (0.5 min.)→72° C. (1.5 min.) was repeated ten times, followed by the cycle of 97° C. (0.25 min.) )→55° C. (0.5 min.)→72° C. (2.5 min.) repeated twenty times. Further, it was maintained at 72° C. for 7 minutes.

Thereafter, a part of the PCR reaction solution was subjected to agarose gel electrophoresis. A band of a DNA fragment of about 1000 bp was detected.

Two types of restriction enzymes (NcoI and BamHI) were added to the remaining PCR reaction solution, and the DNA fragment of about 1000 bp was subjected to double digestion, followed by purification of the enzyme digested DNA fragment.

The plasmid vector pTV118N (Takara Shuzo Co, Ltd.) was digested by two types of restriction enzymes (NcoI and BamHI), and the digested DNA fragments were then purified.

The DNA fragments subjected to enzyme digestion were mixed and were ligated by T4 DNA ligase. *E. coli* DH5 α was transformed by ligation solution obtained in the above step.

The obtained transformant was cultured in a LB agar medium containing 50 µg/ml of ampicillin. Six out of the grown colonies were selected at random. These selected colonies were inoculated into the sterilized LB medium (2 ml) containing 50 µg/ml of ampicillin. It was incubated under shaking in a test tube (at 30° C. for 24 hours). A plasmid was prepared from each cultured bacterial cell using the QIAprep Spin Miniprep Kit (by Qiagen). A portion of the plasmid obtained in the above step was subjected to double digestion by means of two types of restriction enzymes. Then electrophoresis was carried out and all the plasmids were verified to have about 1000 bp of the aforementioned DNA fragments inserted therein. (This plasmid will be described as plasmid pTRPc hereinafter).

(2) *E. coli* HB101 was transformed by plasmid pTRPc. The transformant obtained was inoculated in a sterilized LB medium (100 ml) containing 0.1 mM of 1PTG and 50 µg/ml of ampicillin, and cultivated under shaking (at 30° C. for 12 hours), The obtained cultivation solution was subjected to centrifugal separation to obtain 0.4 g of wet bacterial cells. 300 mg of methyl 4-bromo-3-oxobutanoate, 0.4 g of the aforementioned wet bacterial cells, 9 mg of $NADP^+$, 750 mg of glucose, 1.2 mg of glucose dehydrogenase (by Amano Pharmaceutical Co., Ltd.), 15 ml of 100 mM phosphoric acid buffer solution (pH 6.5) and 15 ml of butyl acetate were mixed and stirred at 30° C. for 7 hours. During stirring, 2M aqueous solution of sodium carbonate was gradually added so that the pH value of the reaction solution is maintained within a range of 6.5±0.2. Then the reaction solution was subjected to centrifugal separation to give an organic layer. This organic layer was subjected to content analysis by gas chromatography under the conditions given below. It was found that methyl 4-bromo-3-hydroxybutanoate was obtained in a yield of 98.5% in terms of the methyl 4-bromo-3-oxobutanoate used for reaction. The optical purity of methyl (S)-4-bromo-3-hydroxybutanoate in the organic layer was measured under the conditions given below and found to be 96.1% e.e. This organic layer was concentrated to obtain crude methyl (S)-4-bromo-3-hydroxybutanoate.

Content Analysis Conditions:

Column: HR-20M (0.53 mm×30 m, 1 µm) (by Shinwa Kako Co., Ltd.)
Column temperature: 120° C. (5 min)→3° C. 150° C. (5 min.)→10° C./min→200° C. (5 min.)
Carrier gas: Helium (flow rate: 20 ml/min.)
Detector: FID Optical Purity Measuring Conditions:

Column: G-TA (0.25 cm×30 m, 0.125 µm) (by Astech, Ltd.)
Column Temperature, 110° C.(20 min)→5° C./min→180° C. (1 min).
Carrier Gas. Helium (Flow rate: 1 ml/min).
Detector: FID
Split ratio: 1/50

The absolute configuration of the product was determined by comparison with an authentic sample of methyl (S)-4-bromo-3-hydroxybutanoate.

EXAMPLE 3

(1) Plasmid pTRPc was subjected to double digestion by means of two types of restriction enzymes (NcoI and BamHI), and the resulting DNA fragments were purified. Plasmid pTrc99A (by Pharmacia) was subjected to double digestion by means of two types of restriction enzymes (NcoI and BamHI), and the resulting DNA fragments were purified.

The digested DNA fragments were mixed and were ligated by T4 DNA ligase. *E. coli* DH5 α was transformed by the ligation solution obtained in the above step.

The transformant obtained was cultivated on a LB medium containing 50 µg/ml of ampicillin. Six out of the grown colonies were selected at random. These selected colonies were inoculated into the sterilized LB medium (2 ml) containing 50 µg/ml of ampicillin. It was incubated under shaking in a test tube (at 30° C. for 24 hours).

Plasmids were prepared from each cultivated bacterial cell using the QIAprep Spin Miniprep Kit (by Qiagen), A portion of the plasmid picked up in the above step was subjected to double digestion by means of two types of restriction enzymes (NcoI and BamHI). Then electrophoresis was carried out and all the plasmids were verified to have the aforementioned DNA fragments of about 1000 bp inserted therein. (This plasmid will be described as plasmid pTrcRPc hereinafter).

(2) *E. coli* HB101 was transformed by plasmid pTrcRPc.

The transformant obtained was cultivated in a sterilized LB medium (100 ml containing 0.1 mM of IPTG and 50 μg/ml of ampicillin. It was incubated under shaking (at 30° C. for 12 hours). The obtained cultivation solution was subjected to centrifugal separation to give 0.4 g of wet bacterial cells. 1500 mg of methyl 4-bromo-3-oxobutanoate, 0.4 g of the aforementioned wet bacterial cells, 18 mg of $NADP^+$, 3000 mg of glucose, 3 mg of glucose dehydrogenase (by Amano Pharmaceutical Co., Ltd.), 15 ml of 100 mM phosphoric acid buffer solution (pH 6.5) and 15 ml of butyl acetate were mixed and stirred at 30° C. for 7 hours. While stirring, 2M aqueous solution of sodium carbonate was gradually added thereto so that the pH of the reaction solution is maintained with in a range of 6.5±0.2. Then the reaction solution was subjected to centrifugal separation to obtain an organic layer. This organic layer was subjected to content analysis under the conditions given in Example 2. It was found that methyl 4-bromo-3-hydroxybutanoate was obtained in a yield of 99.2% based on the consumed methyl 4-bromo-3-oxobutanoate. The optical purity of methyl (S)-4-bromo-3-hydroxybutanoate in the organic layer was measured under the conditions given in Example 2 and found to be 95.7% e.e.

This organic layer was further concentrated to give crude methyl (S) 4-bromo-3-hydroxybutanoate.

EXAMPLE 4

(1) *Bacillus megaterium* IF012108 strain was cultivated in a sterilized LB medium, thereby obtaining 0.4 g of bacterial cells. From these bacterial cells, chromosomal DNA (hereinafter referred to as "chromosome DNA (B)") was purified using the Qiagen Genomic Tip (by Qiagen) according to the method described in the Manual attached thereto.

(2) The oligonucleotide primers of SEQ ID NOs. 25 and 26 were synthesized based on the polynucleotide sequence of the glucose dehydrogenase derived from *Bacillus megaterium* IWG3 described in the Journal of Biological Chemistry Vol. 264, NO:11, 6381–6385(1989).

PCR was conducted using the primers of SEQ ID NOs. 25 and 26 as primers and the aforementioned DNA (B) as a template in the reaction solution of the following composition under the following reaction conditions. (Expand High Fidelity PCR System by Rosche Diagnostic was used.)

Composition of Reaction Solution:

| Chromosome DNA stock solution | 1 μl |
|---|---|
| dNTP (each 2.5 mM-mix) | 0.4 μl |
| Primer (20 pmol/μl) | 0.75 μl each |
| 10 × buffer (with MgCl) | 5 μl |
| enz. expandHiFi (3.5 × $10^3$ U/ml) | 0.375 μl |
| Deionized water | 41.725 μl |

Reaction Conditions:

The reaction vessel containing reaction solution of the aforementioned composition was set to the PERKIN ELMER-GeneAmp PCR System 2400, and was heated at 97° C. (for 2 minutes). Then the cycle of 97° C. (0.25 min)→55° C. (0.5 min.)→72° C. (15.) was repeated ten times, followed by twenty times of a cycle of 97° C. (0.25 mix.)→55° C. (0.5 min.)→72° C. (2.5 min.). Further, it was maintained at 72° C. for 7 minutes.

Thereafter, a portion of the PCR reaction solution was subjected to agarose gel electrophoresis. A band of a DNA fragment of about 950 bp was detected.

Using the PCR reaction solutions obtained in the above step and TOPO™ TA cloning kit by Invitrogen, the DNA fragment of about 950 bp obtained in the aforementioned PCR were ligated to the existing "PCR product insertion site" of the pCR2.1-TOPO vector. The obtained ligation solution was utilized to transform *E. coli* DH5 α.

30 μl of 4% aqueous solution of X-gal and 30 μl of 0.1M IPTG were applied onto the LB agar medium containing 50 μg/ml of ampicillin. The transformant obtained was inoculated thereto, and was incubated. Of the colonies formed, one white colony was picked up and was inoculated into a sterilized LB medium (2 ml) containing 50 μg/ml of ampicillin. It was incubated under shaking in a test tube (at 30° C. for 24 hours). A plasmid was prepared by using the QIAprep Spin Miniprep Kit (by Qiagen) from the cultivated bacterial cells. A portion of the plasmid prepared in the above step was digested with a restriction enzyme (EcoRI). Then electrophoresis was carried out and it was shown that the plasmid has the aforementioned DNA fragment of about 950 bp inserted therein. (This plasmid will be described as plasmid pSDGDH12 hereinafter).

The polynucleotide sequence of the DNA fragment inserted into plasmid pSDGDH12 was analyzed. The result is shown in SEQ ID NO: 27 and its coded peptide SEQ ID NO: 36.

Analysis of the polynucleotide sequence of the DNA fragment inserted into the plasmid was made as follows: Sequence reaction was carried out according to the Dye Terminator Cycle Sequence FS Ready Reaction Kit (by Perkin Elmer) with plasmid pSDGDH12 as a template, and the polynucleotide sequence of the obtained DNA was analyzed by the DNA sequencer 373A (by Perkin Elmer).

(3) Plasmid pSDGDH12 was subjected to double digestion by means of two types of restriction enzymes (BamHI and XbaI), and the resulting DNA fragments were purified.

Plasmid pTrcRPc was subjected to double digestion by means of two types of restriction enzymes (BamHI and XbaI), and the resulting DNA fragments were pied.

Each of the digested DNA fragments was ligated by T4 DNA ligase. *E. coli* DH5 α was transformed by ligation solution obtained in the above step. The transformant obtained was cultivated on a LB medium containing 50 μg/ml of ampicillin. Six out of the grown colonies were selected at random. These selected colonies were inoculated into the sterilized LB medium (2 ml) containing 50 μg/ml of ampicillin. It was incubated under shaking in a test tube (at 30° C. for 24 hours). Plasmid was prepared from each cultivated bacterial cells using the QIAprep Spin Miniprep Kit (by Qiagen). A portion of the plasmid prepared in the above step was subjected to double digestion by means of two types of restriction enzymes (BamHI and XbaI). Then electrophoresis was carried out and all the plasmids were shown to have the inserted DNA fragments of about 1000 bp. (This plasmid will be described as plasmid pTrcRSbG12 hereinafter).

(4) Plasmid pTrcRSbG12 was used to transform *E. coli* HB101. The transformant obtained was inoculated into a sterilized LB medium (100 ml) containing 0.1 mM IPTG and 50 μg/ml of ampicillin. It was incubated under shaking (at 30° C. for 12 hours). The incubated solution was subjected to centrifugal separation, thereby obtaining 0.3 g of wet bacterial cells.

0.3 g of methyl 4-bromo-3-oxobutanoate, 0.3 g of the aforementioned wet bacterial cells, 9 mg of $NADP^+$, 750 mg of glucose, 15 ml of 100 mM phosphate buffer solution (pH 6.5) and 15 ml of butyl acetate were mixed and stirred at 30°

C. for 7 hours. While stirring, 2M aqueous solution of sodium carbonate was gradually added so that the pH of the reaction solution is maintained within a range of 6.5±0.2 Then the reaction solution was subjected to centrifugal separation to give an organic layer. This organic layer was subjected to content analysis under the conditions given in the Example 2. Methyl 4-bromo-3-hydroxybutanoate was found to have been produced in a yield of 99% in terms of methyl 4-bromo-3-oxobutanoate used. The optical purity of methyl (S)-4-bromo-3-hydroxybutanoate in the organic layer was measured under the conditions given in Example 2 and was found to be 96% e.e.

This organic layer was further concentrated to give crude methyl (S)-4-bromo-3-hydroxybutanoate.

EXAMPLE 5

(1) The oligonucleotide primer of SEQ ID NO: 29 was synthesized based on the polynucleotide sequence of SEQ ID NO: 19.

PCR was conducted by using the oligonucleotide primers containing the polynucleotide sequences of SEQ ID NOs. 23 and 29 as primers, and the aforementioned plasmid pTRPc as a template in the reaction solution of the following composition under the following reaction conditions (Expand High Fidelity PCR System by Rosche Diagnostic was used.).

Composition of Reaction Solution:

| Plasmid pTRPc solution | 1 µl |
|---|---|
| dNTP (each 2.5 mM-mix) | 0.4 µl |
| Primer (20 pmol/µl) | 0.75 µl each |
| 10 × buffer (with MgCl) | 5 µl |
| enz. expandHiFi (3.5 × $10^3$ U/ml) | 0.375 µl |
| Deionized water | 41.725 µl |

Reaction Conditions:

The reaction vessel containing reaction solution of the aforementioned composition was set to the PERKIN ELMER-GeneAmp PCR System 2400, and was heated at 97° C. (for 2 minutes). Then a cycle of 97° C. (0.25 min.)→55° C. (0.5 min.)→72° C. (1.5 min.) was repeated ten times, followed by twenty cycles of 97° C. (0.25 min.)→55° C. (0.5 min.)→72° C. (2.5 min.). Further, it was maintained at 72° C. for 7 minutes.

Thereafter, a part of the PCR reaction solution was subjected to agarose gel electrophoresis. A band of a DNA fragment of about 1000 bp was detected. The remaining PCR reaction solution was purified and digested with two types of restriction enzymes (NcoI and BamHI), and the DNA fragment of about 1000 bp was subjected to double digestion, followed by purification of the enzyme digested DNA fragments.

The plasmid vector pTV118N (Takara Shuzo Co., Ltd.) was digested by two types of restriction enzymes (NcoI and BamHI), and the digested DNA fragments were then purified.

The DNA fragments digestion above were mixed and ligated by T4 DNA ligase. E. coli DH5 α was transformed by ligation solution obtained in the above step.

The obtained transformant was cultivated on a LB agar medium containing 50 µg/ml of ampicillin. Six out of the grown colonies were selected at random. These selected colonies were inoculated into the sterilized LB medium (2 ml) containing 50 µg/ml of ampicillin. It was incubated under shaking in a test tube (at 30° C. for 24 hours). A plasmid was prepared from each cultured bacterial cell using the QIAprep Spin Miniprep Kit (by Qiagen). A portion of the plasmid prepared in the above step was subjected to double digestion by means of two types of restriction enzymes (NcoI and BamHI). Then electrophoresis was carried out and all the plasmids were shown to have the aforementioned inserted DNA fragments of about 1000 bp. (This plasmid will be described as plasmid pTRPcS hereinafter). The sequence of the DNA fragment inserted into the plasmid pTRPcS was analyzed, and is shown in SEQ ID NO: 30. Sequence analysis of the DNA fragment was conducted by a sequence reaction using Dye Terminator Cycle sequencing FS ready Reaction Kit (Perkin Elmer) and plasmid pTRPcS as a template, and obtained polynucleotide sequence of the DNA was analyzed by DNA Sequencer 373A (Perkin Elmer).

(2) E. coli HB101 was transformed by plasmid pTRPcS. The transformant obtained was inoculated in a sterilized LB medium (100 ml) containing 0.1 mM of 1PTG and 50 µg/ml of ampicillin, and cultivated under shaking (at 30° C. for 12 hours). The obtained cultivation solution was subjected to centrifugal separation to obtain 0.4 g of wet bacterial cells. 300 mg of methyl 4-bromo-3-oxobutanoate, 0.4 g of the aforementioned wet bacterial cells, 9 mg of $NADP^+$, 750 mg of glucose, 1.2 mg of glucose dehydrogenase (by Amano Pharmaceutical Co., Ltd.), 15 ml of 100 mM phosphoric acid buffer solution (pH 6.5) and 15 ml of butyl acetate were mixed and stirred at 30° C. for 19 hours. While stirring, 2M aqueous solution of sodium carbonate was gradually added thereto so that the pH value of the reaction solution is maintained within a range of 6.5±0.2. Then the reaction solution was subjected to centrifugal separation to give an organic layer. This organic layer was subjected to content analysis by gas chromatography as in Example 2. It was found that methyl 4-bromo-3-hydroxybutanoate was obtained in a yield of 97.3% in terms of the methyl 4-bromo-3-oxobutanoate used for reaction. The optical purity of methyl (S)-4-bromo-3-hydroxybutanoate in the organic layer was measured under the conditions given below and found to be 96.5% e.e. This organic layer is concentrated to give crude methyl (S)-4-bromo-3-hydroxybutanoate.

EXAMPLE 6

(1) The oligonucleotide primers of SEQ ID NOs: 31 and 32 were synthesized based on the polynucleotide sequence of SEQ ID NO: 27.

PCR was conducted by using the oligonucleotide primers of SEQ ID NOs. 31 and 32 as primers, and the aforementioned DNA (B) as a template in the reaction solution of the following composition under the following reaction conditions (Expand High Fidelity PCR System by Rosche Diagnostic was used.).

Composition of Reaction Solution:

| Chromosome DNA stock solution | 1 µl |
|---|---|
| dNTP (each 2.5 mM-mix) | 0.4 µl |
| Primer (20 pmol/µl) | 0.75 µl each |
| 10 × buffer (with MgCl) | 5 µl |
| enz. expandHiFi (3.5 × $10^3$ U/ml) | 0.375 µl |
| Deionized water | 41.725 µl |

Reaction Conditions:

The reaction vessel containing reaction solution of the aforementioned composition was set to the PERKIN ELMER-GeneAmp PCR System 2400, and was heated at 97° C. (for 2 minutes). Then a cycle of 97° C. (0.25 min.)→55° C. (0.5 min.)→72° C. (1.5 min.) was repeated ten times, followed by twenty cycles of 97° C. (0.25 min.)→55° C. (0.5 min.)→72° C. (2.5 min.). Further, it was maintained at 72° C. for 7 minutes.

Thereafter, a part of the PCR reaction solution was subjected to agarose gel electrophoresis. A band of a DNA fragment of about 850 bp was detected. The remaining PCR reaction solution was purified and digested with two types of restriction enzymes (NcoI and BamHI), and the DNA fragment of about 850 bp was subjected to double digestion, followed by purification.

The plasmid vector pTV118N (Takara Shuzo Co., Ltd.) was digested by two types of restriction enzymes (NcoI and BamHI), and the digested DNA fragments were then purified.

The digested DNA fragments above were mixed and ligated by T4 DNA ligase. *E. coli* DH5 α was transformed by ligation solution obtained in the above step.

The obtained transformant was cultivated in a LB agar medium containing 50 μg/ml of ampicillin. Six out of the grown colonies were selected at random. These selected colonies were inoculated into the sterilized LB medium (2 ml) containing 50 μg/ml of ampicillin. It was incubated under shaking in a test tube (at 30° C. for 24 hours). A plasmid was obtained from each cultured bacterial cell using the QIAprep Spin Miniprep Kit (by Qiagen). A portion of the plasmid obtained in the above step was subjected to double digestion by means of two types of restriction enzymes (NcoI and BamHI). Then electrophoresis was carried out and all the plasmids were shown to have the aforementioned inserted DNA fragments of about 850 bp. (This plasmid will be described as plasmid pTGDH 12 hereinafter).

(2) The oligonucleotide primers of SEQ ID NO. 33 was synthesized based on the polynucleotide sequence of plasmid vector pTV118N (by Takara Shuzo, Co., Ltd). PCR reaction was conducted by using the oligonucleotide primers of SEQ ID NO: 32 and NO: 33 as primers and plasmid pTGH12 as a template in the reaction solution of the following composition under the following reaction conditions.

Composition of Reaction Solution:

| | |
|---|---|
| Plasmid pTGDH12 solution | 1 μl |
| dNTP (each 2.5 mM-mix) | 0.4 μl |
| Primer (20 pmol/μl) | 0.75 μl each |
| 10 × buffer (with MgCl) | 5 μl |
| enz. expandHiFi (3.5 × 10³ U/ml) | 0.375 μl |
| Deionized water | 41.725 μl |

Reaction Conditions:

The reaction vessel containing reaction solution of the aforementioned composition was set to the PERKIN ELMER-GeneAmp PCR System 2400, and was heated at 97° C. (for 2 minutes) Then a cycle of 97° C. (0.25 min.)→55° C. (0.5 min.)→72° C. (1.5 min.) was repeated ten times, followed by twenty cycles of 97° C. (0.25 min.)→55° C. (0.5 min.)→72° C. (2.6 min.). Further, it was maintained at 72° C. for 7 minutes.

Thereafter, a portion of the PCR reaction solution was subjected to agarose gel electrophoresis. A band of a DNA fragment of about 1000 bp was detected. The obtained DNA fragment of about 1000 bp was ligated to an existing PCR Product insertion site of pCR2.1-TOPO vector using the PCR solution obtained above and TOPO™ TA cloning kit VER. Eby Invitrogen Co., Ltd, and *E.coli* DH5 α was transformed with the ligation solution.

30 μl of 4% aqueous solution of X-gal and 30 μl of 0.1M IPTG were applied onto the LB agar medium containing 50 μg/ml of ampicillin. The transformant obtained was inoculated thereto, and was incubated. Of the colonies formed, one white colony was picked up and was inoculated into a sterilized LB medium (2 ml) containing 50 μg/ml of ampicillin. It was incubated under shaking in a test tube (at 30° C. for 24 hours). A plasmid was prepared from using the QIAprep Spin Miniprep Kit (by Qiagen) from the cultivated bacterial cells. A portion of the plasmid prepared in the above step was digested with a restriction enzyme (BamHI). Then electrophoresis was carried out and it was shown that the plasmid has the aforementioned inserted DNA fragment of about 1000 bp. (This plasmid will be described as plasmid pCGDH12 hereinafter).

(3) Plasmid pCGDH12 was subjected to digestion by means of restriction enzymes (BamHI), and the resulting DNA fragment of about 1000 bp was purified.

Plasmid vector pACYC184 (Nippon Gene Co., Ltd.) was subjected to digestion of a restriction enzyme (BamHI), and the resulting DNA fragments were purified, and further dephosphorylated with Alkaline Phosphatase (Takara Shuzo Co., Ltd) to prevent self-ligation.

The digested DNA fragments above were mixed and ligated by T4 DNA ligase. *E coli* DH5 α was transformed by ligation solution obtained in the above step. The transformant obtained was cultivated on LB agar medium containing 20 μg/ml of chloramphenicol. Four out of the grown colonies were selected at random. These selected colonies were inoculated into the sterilized LB medium (2 ml) containing 20 μg/ml of chloramphenicol. It was incubated under shaking in a test tube (at 30° C. for 24 hours). Plasmid was prepared from each cultivated bacterial cells using the QIAprep Spin Miniprep Kit (by Qiagen). A portion of the plasmid prepared in the above step was subjected to digestion by a restriction enzyme (BamHI). Then electrophoresis was carried out and all the plasmids were shown to have the inserted DNA fragments of about 1000 bp. (This plasmid will be described as plasmid pAGDH12 hereinafter).

(4) Plasmids pTRPc and pAGDH12 were used to transform *E. coli* HB101. The transformant obtained was inoculated into a sterilized LB medium (100 ml) containing 0.1 mM IPTG and 50 μg/ml of ampicillin and 20 μg/ml of chloramphenicol. It was incubated under shaking (at 30° C. for 18 hours). The incubated solution was subjected to centrifugal separation, thereby obtaining 0.4 g of wet bacterial cells.

0.3 g of methyl 4-bromo-3-oxobutanoate, 0.4 g of the aforementioned wet bacterial cells, 9 mg of NADP$^+$, 750 mg of glucose, 15 ml of 100 mM phosphate buffer solution (pH 6.5) and 15 ml of butyl acetate were mixed and stirred at 30° C. for 19 hours. While stirring, 2M aqueous solution of sodium carbonate was gradually added so that the pH of the reaction solution is maintained within a range of 6.5±0.2. Then the reaction solution was subjected to centrifugal separation to give an organic layer. This organic layer was subjected to content analysis under the conditions given in the Example 2. Methyl 4-bromo-3-hydroxybutanoate was found to have been produced in a yield of 98.6% in terms of methyl 4-bromo-3-oxobutanoate used. The optical purity of methyl (S)-4-bromo-3-hydroxybutanoate in the organic layer was measured under the conditions given in Example 2 and was found to be 96.2% e.e.

This organic layer is further concentrated to give crude methyl (S)-4-bromo-3-hydroxybutanoate.

EXAMPLE 7

Into a 500 ml Sakaguchi flask was placed 100 ml of a sterilized medium (prepared by dissolving 200 g of potato extract and 20 g of dextrose in 1 L of water) and inoculated with cells of *Penicillium citrinum* IFO 4631. Culturing was carried out under aerobic conditions at 30° C. with shaking. The culture was then centrifuged to harvest cells, and the harvested cells were suspended in 5 ml of saline. To this cell suspension was added 300 ml of cold acetone, and the cells were filtered. The resulting cells were dried under vacuum to obtain acetone-dried cells of *Penicillium citrinum* IFO 4631.

To 15 mg of the acetone-dried cells of *Penicillium citrinum* IFO 4631 described above were added 1.5 ml of butyl acetate in which 15 mg of methyl 4-bromo-3-oxobutanoate was dissolved and 1.5 ml of 100 mM phosphate buffer, pH 6.5, in which 75 mg of glucose, 9 mg of NADP$^+$, and 15 U of glucose dehydrogenase were dissolved, and the mixture was shaked at 30° C. for 18 hours. The reaction mixture was then centrifuged to separate the organic layer. The organic layer was analyzed for the content with gas chromatography, and it was confirmed that 5.5 mg of methyl 4-bromo 3-hydroxybutanoate was formed.

Analysis Conditions for Content:
Column: HR-20M (0.53 mm×30 m, 1 μm) (manufactured by Shinwa Kako, Ltd.).
Column Temperature: 120° C. (5 min.)→3° C./min.→150° C. (5 min.)→10° C./min.→200° C. (5 min.).
Carrier Gas: helium (flow rate: 20 ml/min.).
Detector: FID.

Then, the methyl 4-bromo-3-hydroxybutanoate isolated by concentrating the organic layer under vacuum was dissolved in dichloromethane, and trifluoroacetic anhydride was added, The mixture was allowed to stand at room temperature for one hour. This solution was analyzed under the optical isomer analysis conditions described below, and it was determined that the resulting methyl (S)-4-bromo-3-hydroxybutanoate was 98% e.e.

Analysis Conditions for Optical Isomers:
Column: Chirasil-DEX CB (0.32 mm×25 m, 0.25 μm) (manufactured by CHROMPACK, Ltd.).
Column Temperature: 80° C. (20 min.)→7° C./min.→150° C. (5 min.).
Carrier Gas: Helium (flow rate: 1.25 ml/min.).
Detector: FID.

In this case, the absolute configuration of the product was determined by comparison with the authentic sample of methyl (S)-4-bromo-3-hydroxybutanoate.

EXAMPLE 8

Into a 500 ml Sakaguchi flask was placed 100 ml of a sterilized medium (prepared by dissolving 200 g of potato extract and 20 g of dextrose in 1 L of water) and inoculated with cells of *Cryptococcus humicolus* IFO 1527. Cultivation was carried out under aerobic conditions at 30° C. under shaking. The cultivate was then centrifuged to harvest cells, and the harvested cells were suspended in 5 ml of saline. To this cell suspension was added 300 ml of cold acetone, and the cells were filtered. The resulting cells were dried under vacuum to obtain acetone-dried cells of *Cryptococcus humicolus* IFO 1527.

To 15 mg of the acetone-dried cells of *Cryptococcus humicolus* IFO 1527 were added 1.5 ml of butyl acetate in which 15 mg of methyl 4-bromo-3-oxobutanoate was dissolved and 1.5 ml of 100 mM phosphate buffer, pH 6.5, in which 75 mg of glucose, 9 mg of NADP$^+$, and 15 U of glucose dehydrogenase were dissolved, and the mixture was shaked at 30° C. for 18 hours. The reaction mixture was then centrifuged to separate the organic layer. The organic layer was analyzed for the content with gas chromatography, and it was confirmed that 2.0 mg of methyl 4-bromo-3-hydroxybutanoate was formed.

Next, the methyl 4-bromo-3-hydroxybutanoate isolated by concentrating the organic layer under vacuum was dissolved in dichloromethane, and trifluoroacetic anhydride was added. The mixture was allowed to stand at room temperature for one hour. This solution was analyzed under the same optical isomer analysis conditions as in Example 7, and it was determined that the resulting methyl (S)-4-bromo-3-hydroxybutanoate was 88% e.e.

EXAMPLE 9

Into a 500 ml Sakaguchi flask was placed 100 ml of a sterilized medium (prepared by dissolving 20 g of glucose, 5 g of polypeptone, 3 g of yeast extract, 3 g of meat extract, 1 g of potassium dihydrogen phosphate, 0.5 g of magnesium sulfate heptahydrate, and 2 g of ammonium sulfate in 1 L of water) and inoculated with 0.3 ml cultivated product of *Bacillus alvei* IFO 3343t which had been pre-cultivated in a medium having the same composition. Cultivation was carried out at 30° C. for two days under shaking. The cultivated product was then centrifuged to harvest cells, and the harvested cells were washed with saline and then suspended in 5 ml of saline. To this cell suspension was added 300 ml of cold acetone, and the cells were filtered. The resulting cells were dried under vacuum to obtain acetone-dried cells of *Bacillus alvei* IFO 3343t.

To 15 mg of the acetone-dried cells of *Bacillus alvei*IFO 3343t described above were added 1.5 ml of butyl acetate in which 15 mg of methyl 4-bromo-3-oxobutanoate was dissolved and 1.5 ml of 100 mM phosphate buffer, pH 6.5, in which 75 mg of glucose, 9 mg of NAD$^+$, and 15 U of glucose dehydrogenase were dissolved, and the mixture was shaked at 30° C. for 18 hours. The reaction mixture was then centrifuged to separate the organic layer.

The content of the product in the organic layer was analyzed with gas chromatography, and it was found that 4.5 mg of methyl 4-bromo-3-hydroxybutanoate was formed.

Next, the methyl 4-bromo-3-hydroxybutanoate isolated by concentrating the organic layer under reduced pressure was dissolved in dichloromethane, and trifluoroacetic anhydride was added thereto. The mixture was allowed to stand at room temperature for one hour. This solution was analyzed under the same analysis conditions as in Example 7, and it was determined that the purity of the resulting methyl (R)-4-bromo-3-hydroxybutanoate was 96% e.e.

EXAMPLE 10

Into a 30 l jar fermenter was placed 18 l of a sterilized medium (prepared by dissolving 20 g of glucose, 5 g of polypeptone, 3 g of yeast extract, 3 g of meat extract, 1 g of potassium dihydrogen phosphate, 0.5 g of magnesium sulfate heptahydrate, and 2 g of ammonium sulfate in 1 L of water) and added 180 ml culture of *Bacillus alvei* IFO 3343t which had been pre-cultivated in a medium having the same composition. Cultivation was carried out at 30° C. for two days under shaking. The cultivated product was then centrifuged to harvest cells. The harvested cells were washed with saline and then suspended in saline. To this cell suspension was added cold acetone, and the cells were filtered, The resulting cells were dried under vacuum to obtain acetone-dried cells of Bacillus alvei IFO 3343t.

To 750 mg of the acetone-dried cells of Bacillus alvei IFO 3343t described above were added 150 mg of ethyl 4,4,4-trifluoro-3-oxobutanoate and 30 ml of 100 mM phosphate buffer, pH 6.5, in which 750 mg of glucose, 9 mg of NAD+, and 2.25 mg (70 U/mg) of glucose dehydrogenase were dissolved, and the mixture was shaken at 30° C. for 27 hours. Later, ethyl acetate was added, and then centrifuged.

The organic layer was analyzed with gas chromatography, and it was found that 114 mg of ethyl 4,4,4-trifluoro-3-hydroxybutanoate was formed.

(Analysis Conditions for Content)
Column. DB-1 (0.53 mm×30 m, 1.5 μm).
Column Temperature: 40° C. (5 min.)→4° C./min.→60° C. (0 min.)→30° C./min.→290° C. (2 min.).
Carrier Gas: Helium (low rated 20 ml/min.).
Detector: FID.

Next, the ethyl 4,4,4-trifluoro-3-hydroxybutanoate isolated by concentrating the organic layer under reduced pressure was dissolved in dichloromethane, and trifluoroacetic anhydride was added thereto. The mixture was allowed to stand at room temperature for one hour. This solution was analyzed under the same analysis conditions described below, and it was determined that the purity of the resulting ethyl (R)-4,4,4-trifluoro-3-hydroxybutanoate was 99% e.e.

(Analysis Conditions for Optical Isomers)
Column: GAMMMA DEX 120 (0.25 mm×30 m, 0.25 μm) (manufactured by SUPELCO, Ltd.).
Column Temperature: 80° C. (5 min.)→5° C./min.→130° C.→20° C./min.→200° C. (5 min.)
Carrier Gas: Helium (flow rate: 1.25 ml/min.).
Detector: FID.

EXAMPLE 11

Into a flask was placed 900 ml of liquid medium (prepared by dissolving 10 g of tryptone, 5 g of yeast extract, and 5 g of sodium chloride in 1000 ml of water, and adding dropwise 1 N aqueous sodium hydroxide solution to adjust the pH to 7.0) and sterilized, and then ampicillin and isopropyl thio-β-D-galactoside (IPTG) were added to make a concentration of 100 μg/ml and 0.4 mM, respectively. This medium was inoculated with 1 ml of the cultivated liquid resulting from cultivation, in the liquid medium having the above-mentioned composition, a transformed E. coli strain JM109/pUAR obtained by transforming an E. coli strain JM109 by a conventional method using plasmid pUAR containing the DNA shown in SEQ ID NO: 35 (Deposition No. FERM BP-7752 undr the Butapest Treaty), and cultivated at 37° C. for 14 hours with shaking. The culture was centrifuged (15000×g, 15 minutes, 4° C.) to harvest cells, which were suspended in 30 ml of 50 mM monopotassium phosphate-dipotassium phosphate buffer (pH 7.0), followed by centrifugation (15000×g, 15 minutes, 4° C.) to obtain washed cells.

To 50 ml of 50 mM monopotassium phosphate-dipotassium phosphate buffer (pH 7.0) containing 5% of 2-propanol were added 0.1 mmol of NAD+ and 6 g of the washed cells described above. To this mixture was added 50 ml of decane containing 70 mg (0.31 mmol) of isopropyl 4-bromo-3-oxobutanoate, and the mixture was stirred at room temperature for a night and day. Celite was then put into the reaction solution, and stirred for a while and filtered off to separate the resultant solution. The aqueous layer was further extracted three times with ethyl acetate, and combined organic layers were concentrated to give 50 mg of isopropyl 4-bromo-3-hydroxybutanoate.

$^1$H-NMR (CDCl$_3$) δ(ppm): 1.26 (6H), 2.60 (2H), 3.21 (1H), 3.50 (2H), 4.19–4.28 (1H), 5.02–5.11 (1H). Chemical purity: 99% (GC). Optical purity: 77% e.e. (HPLC, a Daicel chiralcel OD column. Mobile phase: hexane/isopropanol=98/2 plus 0.1% trifluoroacetic acid, 0.5 ml/min., W 220 nm). Retention time: 21 minutes.

The following describes Reference Example for producing the authentic sample for determining the optical purity of isopropyl 4-bromo-3-hydroxybutanoate.

REFERENCE EXAMPLE 2

Twenty-three grams of isopropyl 3-oxobutanoate was dissolved in methylene chloride, and 26 g of bromine was added dropwise while cooling it on ice. The mixture was heated to room temperature and stirred for 8 hours, after which the reaction solution was concentrated to 35 g of isopropyl 4-bromo-3-hydroxybutanoate.

Four grams of isopropyl 4-bromo-3-hydroxybutanoate was dissolved in 50 ml of ethanol, and while cooling it on ice, a suspension of 4.04 g of sodium boron hydride in 10 ml of ethanol was slowly added dropwise. After adding was completed, acetic acid was added to the reaction solution, water layer and ethyl acetate layer were separated. The organic layer was dried over anhydrous sodium sulfate, and concentrated. The resulting residue was subjected to a column chromatography on silica gel (developing solvent; hexane/ether) to give 1.3 g of isopropyl 4-bromo-3-hydroxybutanoate.

$^1$H-NMR (CDCl$_3$) δ(ppm): 1.26 (6H), 2.60 (2H), 3.21 (1H), 3.50(2H), 4,19–4.28 (1H), 5.02–5.11 (1H).

The resulting isopropyl 4-bromo-3-hydroxybutanoate was analyzed by HPLC using a Daicel chiralcel OD column (mobile phase: hexane/2-propanol=98/2 plus 0.1% trifluoroacetic acid, 0.5 ml/min., a UV detector at 220 nm), giving an almost equal area ratio of two peaks at a retention time of 19 and 21 minutes

EXAMPLE 12

1.6 g of calcium chloride (15 mmol) and 0.6 g (8.1 mmol) of calcium hydroxide were dissolved in 3.7 ml of water and stirred at room temperature for 20 minutes. At the same temperature, 2.00 g (10 mmol) of methyl 4-bromo-3-hydroxybutanoate was added dropwise over 5 minutes. After stirring for further ten minutes, the mixture was cooled by ice, and 0.6 g (12 mmol) of sodium cyanide was added thereto. Then, the mixture was stirred at an internal temperature of 25 to 33° C. for 4.5 hours. Then, concentrated hydrochloric acid was added dropwise in the reaction solution, and ethyl acetate was used for extraction five times. The organic layer was concentrated under reduced pressure to get 1.2 g of 4-cyano-3-hydroxybutanoic acid. The purity of the obtained 4-cyano-3-hydroxybutanoic acid was 91% (high-performance liquid chromatography in area percentage).

EXAMPLE 13

35 g of 4-cyano-3-hydroxybutanoic acid was dissolved in 250 g of ethyl acetate, and 41 g of triethylamine and 54 g of diethyl sulfate were added thereto at room temperature. Then, the mixture was stirred at an internal temperature of 55 to 60° C. for 30 minutes. After the reaction solution was left cooled down to room temperature, it was added to a saturated sodium bicarbonate solution, and ethyl acetate was used for extraction. The organic layer was washed with saturated saline solution, and the residue obtained by concentrating under reduced pressure was subjected to distillation under reduced pressure, whereby 24.5 g of ethyl 4-cyano-3-hydroxybutanoate was obtained. The purity of the obtained ethyl 4-cyano-3-hydroxybutanoate was 99% (gas chromatography in area percentage).

EXAMPLE 14

22.8 g (205 mmol) of calcium chloride and 8.4 g (114 mmol) of calcium hydroxide were dissolved in 50 g of water and stirred for 20 minutes. Then, 28.0 g (142 mmol) of methyl 4-bromo-3-hydroxybutanoate was added dropwise at room temperature over 5 minutes. The mixture was stirred at room temperature for 10 minutes and then cooled by ice, and 8.7 g (178 mmol) of sodium cyanide was added thereto. Then, the mixture was further stirred at an internal temperature of 25 to 33° C. for 4.5 hours. Then, concentrated hydrochloric acid was added dropwise, and ethyl acetate was used for extraction five times. The residue that was obtained by concentrating the organic layer under reduced pressure was dissolved in ethyl acetate and dried over anhydrous magnesium sulfate. The solution from which magnesium sulfate was removed through filtration was cooled with ice, and 20.0 g (198 mmol) of triethylamine and 26.6 g (172 mmol) of diethyl sulfate were added thereto. It was stirred for about 30 minutes while gradually heating to room temperature. It was further stirred at an internal temperature of 55 to 63° C. for 40 minutes. Then, the reaction solution was cooled by ice and 50 ml of saturated sodium hydrogen carbonate was added thereto, which was then stirred. This solution was separated, and solution layer was subjected again to extraction with ethyl acetate. Combined organic layers were washed with saturated saline solution dried over anhydrous magnesium sulfate, and concentrated. The residue was subjected to the distillation under reduced pressure and 15.7 g of ethyl 4-cyano-3-hydroxybutanoate was obtained. The purity of the obtained ethyl 4-cyano-3-hydroxybutanoate was 95% (gas chromatography in area percentage).

EXAMPLE 15

Into a 500 ml Sakaguchi flask was placed 100 ml of a sterilized medium (prepared by dissolving 200 g of potate extract and 20 g of dextrose in 1 L of water) and inoculated with 0.3 ml cultivated product of Penicillium citrinum IFO 4631. Cultivation was aerobically carried out at 30° C. under shaking. The cultivated product was then centrifuged to harvest cells, and the harvested cells were washed with saline. To this cell suspension was added 300 ml of cold acetone, and the cells were collected by filtration. The collected cells were dried at room temperature under vacuum to obtain acetone-treated cells of Penicillium citrinum IFO 4631. The same procedure was repeated 15 times to give 150 g of the acetone-treated cells of Penicillium citrinum IFO 4631

A solution was prepared by dissolving 75 g of glucose, 0.85 g of oxidized form of nicotine adenine dinucleotide phosphate, 0.11 g of glucose dehydrogenase (glucose amino 2; by Amano enzyme) in 1500 g of a phosphate buffer solution (pH 6.5) and 1300 g of butyl acetate and 37 g of methyl 4-bromo-3-oxobutanoate were added thereto, and then 150 g of the acetone-treated cells of Penicillium citrinum IFO 463described above were added to thereto under stirring. 15% aqueous sodium carbonate solution was dropwise added thereto so that the pH of the reaction solution is maintained within a range of from 6.5±0.5. After stirring for 24 hours, 90 g of celite were added thereto and filtered under reduced pressure. The organic layer separated from the filtrate was concentrated under reduced pressure to give 28 g of methyl (S)-4-bromo-3-hydroxybutanoate, Chemical Purity: 88%, Optical purity: 97% e.e.

Analysis of Chemical Purity:

Column-HR-20M (0.53 mm×30 m, 1 $\mu$m) (manufactured by Shinwa Kako, Ltd.).
Column Temperature: 120° C. (5 min.)→3° C./min. 150° C. (5 min.)→10° C./min.→200° C. (5 min.).
Carrier Gas: helium (flow rate: 20 ml/min.).
Detector: FID.

Analysis of Optical Purity:

High performance Liquid chromatography
Column: Daicel chiralcel OD column (4.6 mm$\phi$×25 cm, 10 $\mu$m)
Mobile phase: hexane/2-propanol, 0.5 $\mu$ml/min.,
Column Temperature: 400° C.,
Detector: UV (220 nm)

23 g of calcium chloride and 8.4 g of calcium hydroxide were dissolved in 50 g of water and stirred for 20 minutes. Then, 28.0 g of methyl (S)-4-bromo-3-hydroxybutanoate obtained above was added dropwise at room temperature over 5 minutes. The mixture was stirred at room temperature for 10 minutes and then cooled by ice, and 8.7 g of sodium cyanide was added thereto. Then, the mixture was farther stirred at an internal temperature of 25 to 33° C. for 4.5 hours. Then, concentrated hydrochloric acid was added dropwise to the reaction solution to make the pH thereof less than 1, and extracted with ethyl acetate five times. The combined organic layers were concentrated under reduced pressure to give a residue, which was dissolved in ethyl acetate and dried over anhydrous magnesium sulfate. Magnesium sulfate was removed by filtration to give a solution of (R)-4-cyano-3-hydroxybutanoic acid.

The solution was cooled with ice, and 20.0 g (198 mmol) of triethylamine and 27 g of diethyl sulfate were added thereto. It was stirred for about 30 minutes while gradually heating to room temperature. It was further stirred at an internal temperature of 55 to 63° C. for 40 minutes. Then, the reaction solution was cooled by ice and 50 ml of saturated sodium hydrogen carbonate was added thereto, and separated.

Aqueous layer was again extracted with ethyl acetate. Combined organic layers were washed with saturated saline solution dried over anhydrous magnesium sulfate, and concentrated. The residue was concentrated under reduced pressure to give 14 g of ethyl (R)-4-cyano-3-hydroxybutanoate. (Purity: 95%, Optical purity 97% e.e.)

MS (EI, m/z): 157M$^+$), $^1$H-NMR (CDCl$_3$) $\delta$(ppm): 1.29 (t, 6H), 2.57–2.71(m, 4H), 3.57(d, 1H), 4.20(q2H), 4.30–4.39(m, 1H). [$\alpha$]$_D^{25}$–28° (c: 1.02, CHCl$_3$)

"Free text for sequence table"

SEQ ID NO: 8
Oligonucleotide primer designed for PCR
SEQ ID NO: 9

Oligonucleotide primer designed for PCR
SEQ ID NO: 10
Oligonucleotide primer designed for PCR
SEQ ID NO: 11
Oligonucleotide primer designed for PCR
SEQ ID NO: 12
Oligonucleotide primer designed for PCR
SEQ ID NO: 13
Oligonucleotide primer designed for PCR
SEQ ID NO: 14
Oligonucleotide primer designed for PCR
SEQ ID NO: 16
Oligonucleotide primer designed for PCR
SEQ ID NO: 17
Oligonucleotide primer designed for PCR
SEQ ID NO: 20
Oligonucleotide primer designed for PCR
SEQ ID NO: 21
Oligonucleotide primer designed for PCR
SEQ ID NO: 23
Oligonucleotide primer designed for PCR
SEQ ID NO: 24
Oligonucleotide primer designed for PCR
SEQ ID NO: 25
Oligonucleotide primer designed for PCR
SEQ ID NO: 26
Oligonucleotide primer designed for PCR
SEQ ID NO: 27
Oligonucleotide primer designed for PCR
SEQ ID NO: 28
Oligonucleotide primer designed for PCR
SEQ ID NO: 29
Oligonucleotide primer designed for PCR
SEQ ID NO: 30
Oligonucleotide primer designed for PCR
SEQ ID NO: 31
Oligonucleotide primer designed for PCR
SEQ ID NO: 32
Oligonucleotide primer designed for PCR
SEQ ID NO: 33

What is claimed is:

1. An isolated polynucleotide sequence containing:
   a) a polynucleotide sequence coding for an amino acid sequence represented by SEQ ID NO: 1;
   b) a polynucleotide sequence coding for an enzyme capable of preferentially producing (S)-4-bromo-3-hydroxybutanoate by asymmetrically reducing 4-bromo-3-oxobutanotate, wherein said polynucleotide sequence hybridizes, under high ion concentrations of 900 mM sodium chloride and 90 mM sodium citrate at 65° C. and the hybrid formed is maintained as a hybrid after being kept at 65° C. for 30 minutes under a low ion concentration of 15 mM sodium chloride and 1.5 mM sodium citrate, to a polynucleotide sequence encoding SEQ ID NO: 1;
   c) a polynucleotide sequence represented by SEQ ID NO: 2;
   d) a polynucleotide sequence coding for an amino acid sequence comprising SEQ ID NO: 1 having additional 6 amino acids of Trp-Ile-Ser-Thr-Lys-Leu SEQ ID NO: 37 at the C-terminal of the amino acid sequence; or
   e) a polynucleotide sequence coding for an an enzyme capable of preferentially producing (S)-4-bromo-3-hydroxybutanoate by asymmetrically reducing 4-bromo-3-oxobutanoate, wherein said polynucleotide sequence hybridizes, under high ion concentrations of 450 to 900 mM sodium chloride and 45 to 90 mM sodium citrate at 65° C. and the hybrid formed is maintained as a hybrid after being kept at 65° C. for 30 minutes under a low ion concentration of 15 to 300 mM sodium chloride and 1.5 to 30 mM sodium citrate and 0.1 to 1.0 wt % of SDS, to a polynucleotide sequence encoding SEQ ID NO:1.

2. A DNA construct comprising a promoter in operative linkage with the polynucleotide sequence as defined in claim 1.

3. A recombinant vector containing the polynucleotide sequence as defined in claim 1 or 2.

4. A process for producing a transformant, which comprises the step of introducing the recombinant vector as defined in claim 3 into a host cell.

5. A transformant having the polynucleotide as defined in claim 1.

6. A transformant having the vector as defined in claim 3.

7. A transformant having the DNA construct as defined in claim 2.

8. A transformant according to claim 7, wherein the transformant is a microorganism.

9. A transformant according to claim 8, wherein the microorganism is *E. coli*.

10. A recombinant vector containing
    A) a polynucleotide construct as defined in claim 1, and
    B) a polynucleotide coding for an enzyme capable of converting oxidized β-nicotinamide-adenine dinucleotide phosphate into a reduced form, wherein the enzyme is glucose dehydrogenase derived from *Bacillus megaterium*.

11. A vector according to claim 10, wherein the enzyme is glucose dehydrogenase derived from *Bacillus megaterium* IFO12108.

12. A transformant having the vector according to claim 10.

13. A transformant according to claim 12, wherein the host is a microorganism.

14. A transformant according to claim 13, wherein the microorganism is *E. coli*.

15. A transformant having

A) the polynucleotide as defined in claim 1, and

B) a polynucleotide coding for an enzyme capable of converting oxidized β-nicotinamide-adenine dinucleotide phosphate into a reduced form, wherein the enzyme is glucose dehydrogenase.

16. A transformant according to claim 15, wherein the enzyme is glucose dehydrogenase derived from *Bacillus megaterium*.

17. A transformant according to claim 15, wherein the enzyme is glucose dehydrogenase derived from *Bacillus megaterium* IFO12108.

* * * * *

SEQUENCE LISTING

<160> NUMBER OF SEQ ID NOS: 37

<210> SEQ ID NO 1
<211> LENGTH: 325
<212> TYPE: PRT
<213> ORGANISM: Penicillium citrinum

<400> SEQUENCE: 1

```
Met Ser Asn Gly Lys Thr Phe Thr Leu Ser Asn Gly Val Lys Ile Pro
  1               5                  10                  15

Gly Val Gly Phe Gly Thr Phe Ala Ser Glu Gly Ser Lys Gly Glu Thr
             20                  25                  30

Tyr Thr Ala Val Thr Thr Ala Leu Lys Thr Gly Tyr Arg His Leu Asp
         35                  40                  45

Cys Ala Trp Tyr Tyr Leu Asn Glu Gly Glu Val Gly Glu Gly Ile Arg
     50                  55                  60

Asp Phe Leu Lys Glu Asn Pro Ser Val Lys Arg Glu Asp Ile Phe Val
 65                  70                  75                  80

Cys Thr Lys Val Trp Asn His Leu His Arg Tyr Glu Asp Val Leu Trp
                 85                  90                  95

Ser Ile Asp Asp Ser Leu Lys Arg Leu Gly Leu Asp Tyr Val Asp Met
                100                 105                 110

Phe Leu Val His Trp Pro Ile Ala Ala Glu Lys Asn Gly Gln Gly Glu
            115                 120                 125

Pro Lys Ile Gly Pro Asp Gly Lys Tyr Val Ile Leu Lys Asp Leu Thr
        130                 135                 140

Glu Asn Pro Glu Pro Thr Trp Arg Ala Met Glu Lys Ile Tyr Glu Asp
145                 150                 155                 160

Arg Lys Ala Arg Ser Ile Gly Val Ser Asn Trp Thr Ile Ala Asp Leu
                165                 170                 175

Glu Lys Met Ser Lys Phe Ala Lys Val Met Pro His Ala Asn Gln Ile
            180                 185                 190

Glu Ile His Pro Phe Leu Pro Asn Glu Glu Leu Val Gln Tyr Cys Phe
        195                 200                 205

Ser Lys Asn Ile Met Pro Val Ala Tyr Ser Pro Leu Gly Ser Gln Asn
    210                 215                 220
```

```
Gln Val Pro Thr Thr Gly Glu Arg Val Ser Glu Asn Lys Thr Leu Asn
225                 230                 235                 240

Glu Ile Ala Glu Lys Gly Gly Asn Thr Leu Ala Gln Val Leu Ile Ala
                245                 250                 255

Trp Gly Leu Arg Arg Gly Tyr Val Val Leu Pro Lys Ser Ser Asn Pro
            260                 265                 270

Lys Arg Ile Glu Ser Asn Phe Lys Ser Ile Glu Leu Ser Asp Ala Asp
                275                 280                 285

Phe Glu Ala Ile Asn Ala Val Ala Lys Gly Arg His Phe Arg Phe Val
            290                 295                 300

Asn Met Lys Asp Thr Phe Gly Tyr Asp Val Trp Pro Glu Glu Thr Ala
305                 310                 315                 320

Lys Asn Leu Ser Ala
                325

<210> SEQ ID NO 2
<211> LENGTH: 978
<212> TYPE: DNA
<213> ORGANISM: Penicillium citrinum
<220> FEATURE:
<221> NAME/KEY: CDS
<222> LOCATION: (1)..(975)

<400> SEQUENCE: 2 atg tct aac gga aag act ttc aca ttg agc aac ggc gtc aag att cct    48
Met Ser Asn Gly Lys Thr Phe Thr Leu Ser Asn Gly Val Lys Ile Pro
1               5                   10                  15 ggc gtc ggc ttt ggt acc ttc gct agt gaa ggt tcc aag ggc gag acc    96
Gly Val Gly Phe Gly Thr Phe Ala Ser Glu Gly Ser Lys Gly Glu Thr
            20                  25                  30 tat act gct gtc acc act gcc ctg aag acc ggt tac cgt cac ttg gac   144
Tyr Thr Ala Val Thr Thr Ala Leu Lys Thr Gly Tyr Arg His Leu Asp
        35                  40                  45 tgt gcc tgg tac tac ctg aac gag ggt gag gtt ggt gag ggt atc cgt   192
Cys Ala Trp Tyr Tyr Leu Asn Glu Gly Glu Val Gly Glu Gly Ile Arg
    50                  55                  60 gac ttc ctg aag gag aac ccc tcg gtg aag cgt gag gac atc ttc gtc   240
Asp Phe Leu Lys Glu Asn Pro Ser Val Lys Arg Glu Asp Ile Phe Val
65                  70                  75                  80 tgc acc aag gtg tgg aac cac ctc cac cgt tat gag gac gtc ctc tgg   288
Cys Thr Lys Val Trp Asn His Leu His Arg Tyr Glu Asp Val Leu Trp
                85                  90                  95 tcc att gac gac tcc ctg aag cgt ctt gga ctt gac tac gtt gat atg   336
Ser Ile Asp Asp Ser Leu Lys Arg Leu Gly Leu Asp Tyr Val Asp Met
            100                 105                 110 ttc ctc gtt cac tgg ccc att gct gcc gag aag aat ggc cag ggt gag   384
Phe Leu Val His Trp Pro Ile Ala Ala Glu Lys Asn Gly Gln Gly Glu
        115                 120                 125 ccc aag att ggc cct gac ggc aaa tac gtc att ctc aag gac ctg acc   432
Pro Lys Ile Gly Pro Asp Gly Lys Tyr Val Ile Leu Lys Asp Leu Thr
    130                 135                 140 gag aac ccc gag ccc aca tgg cgc gct atg gag aag att tat gag gat   480
Glu Asn Pro Glu Pro Thr Trp Arg Ala Met Glu Lys Ile Tyr Glu Asp
145                 150                 155                 160 cgc aag gcc agg tcc att ggt gtc tcc aac tgg acc att gcc gac ctt   528
Arg Lys Ala Arg Ser Ile Gly Val Ser Asn Trp Thr Ile Ala Asp Leu
                165                 170                 175 gag aag atg tcc aag ttc gcc aag gtc atg cct cac gcc aac cag atc   576
Glu Lys Met Ser Lys Phe Ala Lys Val Met Pro His Ala Asn Gln Ile
```

-continued

```
                    180                 185                 190
gag att cac ccc ttc ctg ccc aac gag gag ctg gtg cag tac tgc ttc      624
Glu Ile His Pro Phe Leu Pro Asn Glu Glu Leu Val Gln Tyr Cys Phe
        195                 200                 205 tcc aag aac att atg ccc gtg gcc tac tct cct ctg ggc tcg cag aac      672
Ser Lys Asn Ile Met Pro Val Ala Tyr Ser Pro Leu Gly Ser Gln Asn
210                 215                 220 cag gtt ccc acc acc ggt gag cgg gtc agc gag aac aag act ctg aac      720
Gln Val Pro Thr Thr Gly Glu Arg Val Ser Glu Asn Lys Thr Leu Asn
225                 230                 235                 240 gag atc gcc gag aag ggc ggc aac acc ctt gct cag gtt ctt att gcc      768
Glu Ile Ala Glu Lys Gly Gly Asn Thr Leu Ala Gln Val Leu Ile Ala
                245                 250                 255 tgg ggt ctg cgc cgt ggc tac gtc gtt ctc ccc aag agc tcc aac ccc      816
Trp Gly Leu Arg Arg Gly Tyr Val Val Leu Pro Lys Ser Ser Asn Pro
            260                 265                 270 aag cgc att gag tcc aac ttc aag agc att gag ctc tcc gat gcc gac      864
Lys Arg Ile Glu Ser Asn Phe Lys Ser Ile Glu Leu Ser Asp Ala Asp
        275                 280                 285 ttt gaa gcc atc aat gcc gtt gcc aag ggt cgt cac ttc cgt ttc gtc      912
Phe Glu Ala Ile Asn Ala Val Ala Lys Gly Arg His Phe Arg Phe Val
    290                 295                 300 aac atg aag gat act ttc gga tat gat gtc tgg ccc gag gag acc gcc      960
Asn Met Lys Asp Thr Phe Gly Tyr Asp Val Trp Pro Glu Glu Thr Ala
305                 310                 315                 320 aag aac ctg tct gcg tga                                              978
Lys Asn Leu Ser Ala
                325
```

<210> SEQ ID NO 3
<211> LENGTH: 17
<212> TYPE: PRT
<213> ORGANISM: Penicillium citrinum

<400> SEQUENCE: 3

```
Asn Ile Met Pro Val Ala Tyr Ser Pro Leu Gly Ser Gln Asn Gln Val
 1               5                  10                  15
Pro
```

<210> SEQ ID NO 4
<211> LENGTH: 10
<212> TYPE: PRT
<213> ORGANISM: Penicillium citrinum

<400> SEQUENCE: 4

```
Ile Pro Gly Val Phe Gly Thr Phe Ala Ser
 1               5                  10
```

<210> SEQ ID NO 5

<400> SEQUENCE: 5

000

<210> SEQ ID NO 6
<211> LENGTH: 14
<212> TYPE: PRT
<213> ORGANISM: Penicillium citrinum
<220> FEATURE:
<221> NAME/KEY: MOD_RES
<222> LOCATION: (6)..(7)
<223> OTHER INFORMATION: Variable amino acid -continued

```
<400> SEQUENCE: 6

Tyr Glu Asp Val Leu Xaa Xaa Ile Asp Asp Ser Leu Lys Arg
 1               5                  10

<210> SEQ ID NO 7

<400> SEQUENCE: 7

000

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
ggaacytgrt tytggswacc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 9
tangcnacng gcataatatt                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 10
tangcnacng gcataatgtt                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer
```

```
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 11
tangcnacng gcatgatatt                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 12
tangcnacng gcatgatgtt                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 13
tangcnacng gcattatatt                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
```

-continued

<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown

<400> SEQUENCE: 14
tangcnacng gcattatgtt                                               20

<210> SEQ ID NO 15
<211> LENGTH: 697
<212> TYPE: DNA
<213> ORGANISM: Escherichia coli
<220> FEATURE:
<221> NAME/KEY: modified_base
<222> LOCATION: (14)
<223> OTHER INFORMATION: a, c, t, g, other or unknown
<220> FEATURE:
<221> NAME/KEY: modified_base
<222> LOCATION: (63)
<223> OTHER INFORMATION: a, c, t, g, other or unknown
<220> FEATURE:
<221> NAME/KEY: modified_base
<222> LOCATION: (116)
<223> OTHER INFORMATION: a, c, t, g, other or unknown
<220> FEATURE:
<221> NAME/KEY: modified_base
<222> LOCATION: (148)
<223> OTHER INFORMATION: a, c, t, g, other or unknown
<220> FEATURE:
<221> NAME/KEY: modified_base
<222> LOCATION: (185)
<223> OTHER INFORMATION: a, c, t, g, other or unknown
<220> FEATURE:
<221> NAME/KEY: modified_base
<222> LOCATION: (235)
<223> OTHER INFORMATION: a, c, t, g, other or unknown
<220> FEATURE:
<221> NAME/KEY: modified_base
<222> LOCATION: (346)
<223> OTHER INFORMATION: a, c, t, g, other or unknown
<220> FEATURE:
<221> NAME/KEY: modified_base
<222> LOCATION: (460)
<223> OTHER INFORMATION: a, c, t, g, other or unknown
<220> FEATURE:
<221> NAME/KEY: modified_base
<222> LOCATION: (463)
<223> OTHER INFORMATION: a, c, t, g, other or unknown
<220> FEATURE:
<221> NAME/KEY: modified_base
<222> LOCATION: (485)
<223> OTHER INFORMATION: a, c, t, g, other or unknown
<220> FEATURE:
<221> NAME/KEY: modified_base
<222> LOCATION: (489)
<223> OTHER INFORMATION: a, c, t, g, other or unknown
<220> FEATURE:
<221> NAME/KEY: modified_base
<222> LOCATION: (491)
<223> OTHER INFORMATION: a, c, t, g, other or unknown
<220> FEATURE:
<221> NAME/KEY: modified_base
<222> LOCATION: (520)
<223> OTHER INFORMATION: a, c, t, g, other or unknown
<220> FEATURE:
<221> NAME/KEY: modified_base
<222> LOCATION: (524)
<223> OTHER INFORMATION: a, c, t, g, other or unknown
<220> FEATURE:
<221> NAME/KEY: modified_base
<222> LOCATION: (593)
<223> OTHER INFORMATION: a, c, t, g, other or unknown
<220> FEATURE:
<221> NAME/KEY: modified_base
<222> LOCATION: (602)
<223> OTHER INFORMATION: a, c, t, g, other or unknown

```
<220> FEATURE:
<221> NAME/KEY: modified_base
<222> LOCATION: (682)
<223> OTHER INFORMATION: a, c, t, g, other or unknown

<400> SEQUENCE: 15
cgctctaaaa ctantggatc ccccgggctg caggaattcg gcggcggcgg atccaacgga      60
aanactttca cactgagcaa cggcgtcaaa attcctggcg tcggctttgg tacctncgct     120
agtgaaggtt ccaagggcga aacctatnct gctgtcacca ctgccctgaa aaccggttac     180
cgtcncttgg actgtgcctg gtactacctg aacaagggtg aggttggtga gggtntccgt     240
gacttcctga aggaaaaccc ctcggtgaag cgtgaggaca tcttcgtctg caccaaggtg     300
tggaaccacc tccaccgtta tgaggacgtc tctggtcca ttgacnactc cctgaagcgt     360
cttggacttg actacgttga tatgttcctc gttcactggc ccattgctgc cgaaaaaaat     420
ggccagggtg agcccaaaat tggccctgac ggcaaatacn tcnttctcaa ggacctgacc     480
gaaancccna ncccacctgg cgcgctatgg aaaaaatttn tgangatccc aaggccaggt     540
ccattggtgt ttccaattgg accattgccg accttgagaa gatgtccaag ttngccaagg     600
tnatgcctca cgccaaccag atcgagattc acccccttcct gcccaacgag gagctggtgc     660
agtactgctt ttccaagaac antatgcccg tagcgta                              697

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 16
ggaggtggtt ccacaccttg g                                                21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
caaccagatc gagattcacc                                                  20

<210> SEQ ID NO 18
<211> LENGTH: 331
<212> TYPE: DNA
<213> ORGANISM: Escherichia coli
<220> FEATURE:
<221> NAME/KEY: modified_base
<222> LOCATION: (14)
<223> OTHER INFORMATION: a, c, t, g, other or unknown

<400> SEQUENCE: 18
cgctctaaaa ctantggatc ccccgggctg caggaattcg gcggccgcgg atccttcatc      60
cccatcatgt ctaacggaaa gactttcaca ttgagcaacg gcgtcaagat tcctggcgtc     120
ggctttggta ccttcgctag tgaaggttcc aagggcgaga cctatactgc tgtcaccact     180
gccctgaaga ccggttaccg tcacttggac tgtgcctggt actacctgaa cgagggtgag     240
gttggtgagg gtatccgtga cttcctgaag gagaacccct cggtgaagcg tgaggacatc     300
ttcgtctgca ccaaggtgtg gaaccacctc c                                    331
```

-continued

```
<210> SEQ ID NO 19
<211> LENGTH: 743
<212> TYPE: DNA
<213> ORGANISM: Escherichia coli
<220> FEATURE:
<221> NAME/KEY: modified_base
<222> LOCATION: (434)
<223> OTHER INFORMATION: a, c, t, g, other or unknown
<220> FEATURE:
<221> NAME/KEY: modified_base
<222> LOCATION: (440)
<223> OTHER INFORMATION: a, c, t, g, other or unknown
<220> FEATURE:
<221> NAME/KEY: modified_base
<222> LOCATION: (443)
<223> OTHER INFORMATION: a, c, t, g, other or unknown
<220> FEATURE:
<221> NAME/KEY: modified_base
<222> LOCATION: (448)
<223> OTHER INFORMATION: a, c, t, g, other or unknown
<220> FEATURE:
<221> NAME/KEY: modified_base
<222> LOCATION: (458)
<223> OTHER INFORMATION: a, c, t, g, other or unknown
<220> FEATURE:
<221> NAME/KEY: modified_base
<222> LOCATION: (467)
<223> OTHER INFORMATION: a, c, t, g, other or unknown
<220> FEATURE:
<221> NAME/KEY: modified_base
<222> LOCATION: (475)
<223> OTHER INFORMATION: a, c, t, g, other or unknown
<220> FEATURE:
<221> NAME/KEY: modified_base
<222> LOCATION: (506)
<223> OTHER INFORMATION: a, c, t, g, other or unknown
<220> FEATURE:
<221> NAME/KEY: modified_base
<222> LOCATION: (510)
<223> OTHER INFORMATION: a, c, t, g, other or unknown
<220> FEATURE:
<221> NAME/KEY: modified_base
<222> LOCATION: (517)
<223> OTHER INFORMATION: a, c, t, g, other or unknown
<220> FEATURE:
<221> NAME/KEY: modified_base
<222> LOCATION: (522)
<223> OTHER INFORMATION: a, c, t, g, other or unknown
<220> FEATURE:
<221> NAME/KEY: modified_base
<222> LOCATION: (533)
<223> OTHER INFORMATION: a, c, t, g, other or unknown
<220> FEATURE:
<221> NAME/KEY: modified_base
<222> LOCATION: (535)
<223> OTHER INFORMATION: a, c, t, g, other or unknown
<220> FEATURE:
<221> NAME/KEY: modified_base
<222> LOCATION: (583)..(584)
<223> OTHER INFORMATION: a, c, t, g, other or unknown
<220> FEATURE:
<221> NAME/KEY: modified_base
<222> LOCATION: (607)
<223> OTHER INFORMATION: a, c, t, g, other or unknown
<220> FEATURE:
<221> NAME/KEY: modified_base
<222> LOCATION: (616)
<223> OTHER INFORMATION: a, c, t, g, other or unknown
<220> FEATURE:
<221> NAME/KEY: modified_base
<222> LOCATION: (634)
<223> OTHER INFORMATION: a, c, t, g, other or unknown
<220> FEATURE:
<221> NAME/KEY: modified_base
<222> LOCATION: (639)
<223> OTHER INFORMATION: a, c, t, g, other or unknown
<220> FEATURE:
<221> NAME/KEY: modified_base
```

```
<222> LOCATION: (648)
<223> OTHER INFORMATION: a, c, t, g, other or unknown
<220> FEATURE:
<221> NAME/KEY: modified_base
<222> LOCATION: (651)..(652_
<223> OTHER INFORMATION: a, c, t, g, other or unknown
<220> FEATURE:
<221> NAME/KEY: modified_base
<222> LOCATION: (659)
<223> OTHER INFORMATION: a, c, t, g, other or unknown
<220> FEATURE:
<221> NAME/KEY: modified_base
<222> LOCATION: (662)
<223> OTHER INFORMATION: a, c, t, g, other or unknown
<220> FEATURE:
<221> NAME/KEY: modified_base
<222> LOCATION: (664)
<223> OTHER INFORMATION: a, c, t, g, other or unknown
<220> FEATURE:
<221> NAME/KEY: modified_base
<222> LOCATION: (670)..(671)
<223> OTHER INFORMATION: a, c, t, g, other or unknown
<220> FEATURE:
<221> NAME/KEY: modified_base
<222> LOCATION: (690)
<223> OTHER INFORMATION: a, c, t, g, other or unknown
<220> FEATURE:
<221> NAME/KEY: modified_base
<222> LOCATION: (693)
<223> OTHER INFORMATION: a, c, t, g, other or unknown
<220> FEATURE:
<221> NAME/KEY: modified_base
<222> LOCATION: (695)
<223> OTHER INFORMATION: a, c, t, g, other or unknown
<220> FEATURE:
<221> NAME/KEY: modified_base
<222> LOCATION: (702)
<223> OTHER INFORMATION: a, c, t, g, other or unknown
<220> FEATURE:
<221> NAME/KEY: modified_base
<222> LOCATION: (717)
<223> OTHER INFORMATION: a, c, t, g, other or unknown
<220> FEATURE:
<221> NAME/KEY: modified_base
<222> LOCATION: (723)
<223> OTHER INFORMATION: a, c, t, g, other or unknown
<220> FEATURE:
<221> NAME/KEY: modified_base
<222> LOCATION: (728)
<223> OTHER INFORMATION: a, c, t, g, other or unknown
<220> FEATURE:
<221> NAME/KEY: modified_base
<222> LOCATION: (734)
<223> OTHER INFORMATION: a, c, t, g, other or unknown

<400> SEQUENCE: 19
caaccagatc gagattcacc ccttcctgcc caacgaggag ctggtgcagt actgcttctc      60
caagaacatt atgcccgtgg cctactctcc tctgggctcg cagaaccagg ttcccaccac     120
cggtgagcgg gtcagcgaga acaagactct gaacgagatc gccgagaagg gcggcaacac     180
ccttgctcag gttcttattg cctggggtct gcgccgtggc tacgtcgttc tcccaagag      240 ctccaacccc aagcgcattg agtccaactt caagagcatt gagctctccg atgccgactt     300
tgaagccatc aatgccgttg ccaagggtcg tcacttccgt ttcgtcaaca tgaaggatac     360
tttcggatat gatgtctggc ccgaggagac cgccaagaac ctgtctgcgt gaatctctac     420
gaaattataa aatnacaccn acnaaaaancc aaagcganag gatgatnccc aaaanttttg     480
agggtttctt ggttgaaaac gtttantgan cccgaantga angaatagat gancntgatt     540
tctccaaaaa aaaaaaaaaa aaaacggtc cgcggccgct ccnngggggg gcccggttcc      600
caattcnccc cttatnattg aattctttt taangggggnc aaattccncc nnatttccnt     660
```

```
cnanattggn nggccgcctc caaactttcn tcntnaaagg gncccaattc cccccnatt      720 aantggantt cctntttacc ttt                                            743
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20

```
ccaaggtgtg gaaccacctc c                                              21
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21

```
ccagaggaga gtaggccacg g                                              21
```

<210> SEQ ID NO 22
<211> LENGTH: 417
<212> TYPE: DNA
<213> ORGANISM: Escherichia coli

<400> SEQUENCE: 22

```
ccaaggtgtg gaaccacctc caccgttatg aggacgtcct ctggtccatt gacgactccc    60
tgaagcgtct tggacttgac tacgttgata tgttcctcgt tcactggccc attgctgccg    120
agaagaatgg ccagggtgag cccaagattg gccctgacgg caaatacgtc attctcaagg    180
acctgaccga gaaccccgag cccacatggc gcgctatgga gaagatttat gaggatcgca    240
aggccaggtc cattggtgtc tccaactgga ccattgccga ccttgagaag atgtccaagt    300
tcgccaaggt catgcctcac gccaaccaga tcgagattca ccccttcctg cccaacgagg    360
agctggtgca gtactgcttc tccaagaaca ttatgcccgt ggcctactct cctctgg      417
```

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 23

```
gccatggcta tgtctaacgg aaagact                                        27
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24

```
cggatccgtt ataatttcgt agagattca                                      29
```

<210> SEQ ID NO 25
<211> LENGTH: 21
<212> TYPE: DNA
<213> ORGANISM: Artificial Sequence

```
<220> FEATURE:
<223> OTHER INFORMATION: Description of Artificial Sequence: Primer

<400> SEQUENCE: 25
gatcatcata gcaggagtca t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
gaattcaaca ccagtcagct c                                              21

<210> SEQ ID NO 27
<211> LENGTH: 786
<212> TYPE: DNA
<213> ORGANISM: Escherichia coli
<220> FEATURE:
<221> NAME/KEY: CDS
<222> LOCATION: (1)..(783)

<400> SEQUENCE: 27
```

| | | | | | | | | | | | | | | | | |
|---|---|---|---|---|---|---|---|---|---|---|---|---|---|---|---|---|
| atg | tat | aaa | gat | tta | gaa | gga | aaa | gta | gtt | gtc | ata | aca | ggt | tca | tct | 48 |
| Met | Tyr | Lys | Asp | Leu | Glu | Gly | Lys | Val | Val | Val | Ile | Thr | Gly | Ser | Ser | |
| 1 | | | | 5 | | | | | 10 | | | | | 15 | | |
| acc | ggt | tta | gga | aaa | gca | atg | gcg | att | cgt | ttt | gcg | aca | gaa | aaa | gct | 96 |
| Thr | Gly | Leu | Gly | Lys | Ala | Met | Ala | Ile | Arg | Phe | Ala | Thr | Glu | Lys | Ala | |
| | | | 20 | | | | | 25 | | | | | 30 | | | |
| aaa | gta | gtt | gtg | aac | tat | cgt | tcg | aaa | gaa | gaa | gaa | gct | aac | agc | gtt | 144 |
| Lys | Val | Val | Val | Asn | Tyr | Arg | Ser | Lys | Glu | Glu | Glu | Ala | Asn | Ser | Val | |
| | 35 | | | | | 40 | | | | | 45 | | | | | |
| tta | gaa | gaa | att | aaa | aaa | gtg | ggc | gga | gag | gct | att | gcc | gtc | aaa | ggt | 192 |
| Leu | Glu | Glu | Ile | Lys | Lys | Val | Gly | Gly | Glu | Ala | Ile | Ala | Val | Lys | Gly | |
| 50 | | | | | 55 | | | | | 60 | | | | | | |
| gat | gta | aca | gtt | gag | tct | gat | gtg | atc | aat | tta | gtt | caa | tct | gct | att | 240 |
| Asp | Val | Thr | Val | Glu | Ser | Asp | Val | Ile | Asn | Leu | Val | Gln | Ser | Ala | Ile | |
| 65 | | | | | 70 | | | | | 75 | | | | | 80 | |
| aaa | gaa | ttt | gga | aag | cta | gac | gtt | atg | att | aat | aac | gca | gga | atg | gaa | 288 |
| Lys | Glu | Phe | Gly | Lys | Leu | Asp | Val | Met | Ile | Asn | Asn | Ala | Gly | Met | Glu | |
| | | | | 85 | | | | | 90 | | | | | 95 | | |
| aat | ccg | gtt | tcg | tct | cat | gaa | atg | tct | tta | agt | gat | tgg | aat | aaa | gtc | 336 |
| Asn | Pro | Val | Ser | Ser | His | Glu | Met | Ser | Leu | Ser | Asp | Trp | Asn | Lys | Val | |
| | | | 100 | | | | | 105 | | | | | 110 | | | |
| att | gat | acg | aac | tta | acg | gga | gca | ttt | tta | ggc | agc | cgt | gaa | gcg | att | 384 |
| Ile | Asp | Thr | Asn | Leu | Thr | Gly | Ala | Phe | Leu | Gly | Ser | Arg | Glu | Ala | Ile | |
| | 115 | | | | | 120 | | | | | 125 | | | | | |
| aaa | tat | ttt | gtg | gaa | aat | gat | att | aag | gga | aca | gtt | att | aac | atg | tcg | 432 |
| Lys | Tyr | Phe | Val | Glu | Asn | Asp | Ile | Lys | Gly | Thr | Val | Ile | Asn | Met | Ser | |
| 130 | | | | | 135 | | | | | 140 | | | | | | |
| agt | gtt | cac | gag | aaa | att | cct | tgg | cca | tta | ttt | gtt | cat | tac | gca | gca | 480 |
| Ser | Val | His | Glu | Lys | Ile | Pro | Trp | Pro | Leu | Phe | Val | His | Tyr | Ala | Ala | |
| 145 | | | | | 150 | | | | | 155 | | | | | 160 | |
| agt | aaa | ggc | gga | atg | aag | ctc | atg | acc | gaa | aca | ctt | gca | tta | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gct | cca | aaa | ggt | att | cgt | gta | aat | aac | att | gga | ccg | gga | gcg | att | aat | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| aca | ccg | att | aac | gct | gag | aaa | ttt | gct | gat | cct | gag | cag | cgt | gca | gat | 624 |

```
                    Thr Pro Ile Asn Ala Glu Lys Phe Ala Asp Pro Glu Gln Arg Ala Asp
                                195                 200                 205 gta gaa agc atg att cca atg gga tac att gga gag ccg gaa gaa att              672
Val Glu Ser Met Ile Pro Met Gly Tyr Ile Gly Glu Pro Glu Glu Ile
210                 215                 220 gca gcg gtt gct gca tgg cta gct tct tca gag gca agt tat gta aca              720
Ala Ala Val Ala Ala Trp Leu Ala Ser Ser Glu Ala Ser Tyr Val Thr
225                 230                 235                 240 ggg att aca ctc ttt gct gac ggc ggt atg aca cag tac cca tca ttc              768
Gly Ile Thr Leu Phe Ala Asp Gly Gly Met Thr Gln Tyr Pro Ser Phe
                245                 250                 255 caa gca gga cgc gga taa                                                      786
Gln Ala Gly Arg Gly
            260

<210> SEQ ID NO 28
<211> LENGTH: 996
<212> TYPE: DNA
<213> ORGANISM: Penicillium citrinum
<220> FEATURE:
<221> NAME/KEY: CDS
<222> LOCATION: (1)..(975)

<400> SEQUENCE: 28 atg tct aac gga aag act ttc aca ttg agc aac ggc gtc aag att cct              48
Met Ser Asn Gly Lys Thr Phe Thr Leu Ser Asn Gly Val Lys Ile Pro
1               5                   10                  15 ggc gtc ggc ttt ggt acc ttc gct agt gaa ggt tcc aag ggc gag acc              96
Gly Val Gly Phe Gly Thr Phe Ala Ser Glu Gly Ser Lys Gly Glu Thr
                20                  25                  30 tat act gct gtc acc act gcc ctg aag acc ggt tac cgt cac ttg gac              144
Tyr Thr Ala Val Thr Thr Ala Leu Lys Thr Gly Tyr Arg His Leu Asp
            35                  40                  45 tgt gcc tgg tac tac ctg aac gag ggt gag gtt ggt gag ggt atc cgt              192
Cys Ala Trp Tyr Tyr Leu Asn Glu Gly Glu Val Gly Glu Gly Ile Arg
        50                  55                  60 gac ttc ctg aag gag aac ccc tcg gtg aag cgt gag gac atc ttc gtc              240
Asp Phe Leu Lys Glu Asn Pro Ser Val Lys Arg Glu Asp Ile Phe Val
65                  70                  75                  80 tgc acc aag gtg tgg aac cac ctc cac cgt tat gag gac gtc ctc tgg              288
Cys Thr Lys Val Trp Asn His Leu His Arg Tyr Glu Asp Val Leu Trp
                85                  90                  95 tcc att gac gac tcc ctg aag cgt ctt gga ctt gac tac gtt gat atg              336
Ser Ile Asp Asp Ser Leu Lys Arg Leu Gly Leu Asp Tyr Val Asp Met
                100                 105                 110 ttc ctc gtt cac tgg ccc att gct gcc gag aag aat ggc cag ggt gag              384
Phe Leu Val His Trp Pro Ile Ala Ala Glu Lys Asn Gly Gln Gly Glu
            115                 120                 125 ccc aag att ggc cct gac ggc aaa tac gtc att ctc aag gac ctg acc              432
Pro Lys Ile Gly Pro Asp Gly Lys Tyr Val Ile Leu Lys Asp Leu Thr
        130                 135                 140 gag aac ccc gag ccc aca tgg cgc gct atg gag aag att tat gag gat              480
Glu Asn Pro Glu Pro Thr Trp Arg Ala Met Glu Lys Ile Tyr Glu Asp
145                 150                 155                 160 cgc aag gcc agg tcc att ggt gtc tcc aac tgg acc att gcc gac ctt              528
Arg Lys Ala Arg Ser Ile Gly Val Ser Asn Trp Thr Ile Ala Asp Leu
                165                 170                 175 gag aag atg tcc aag ttc gcc aag gtc atg cct cac gcc aac cag atc              576
Glu Lys Met Ser Lys Phe Ala Lys Val Met Pro His Ala Asn Gln Ile
            180                 185                 190 gag att cac ccc ttc ctg ccc aac gag gag ctg gtg cag tac tgc ttc              624
```

```
                                                                                  -continued Glu Ile His Pro Phe Leu Pro Asn Glu Glu Leu Val Gln Tyr Cys Phe
        195                 200                 205 tcc aag aac att atg ccc gtg gcc tac tct cct ctg ggc tcg cag aac        672
Ser Lys Asn Ile Met Pro Val Ala Tyr Ser Pro Leu Gly Ser Gln Asn
    210                 215                 220 cag gtt ccc acc acc ggt gag cgg gtc agc gag aac aag act ctg aac        720
Gln Val Pro Thr Thr Gly Glu Arg Val Ser Glu Asn Lys Thr Leu Asn
225                 230                 235                 240 gag atc gcc gag aag ggc ggc aac acc ctt gct cag gtt ctt att gcc        768
Glu Ile Ala Glu Lys Gly Gly Asn Thr Leu Ala Gln Val Leu Ile Ala
                245                 250                 255 tgg ggt ctg cgc cgt ggc tac gtc gtt ctc ccc aag agc tcc aac ccc        816
Trp Gly Leu Arg Arg Gly Tyr Val Val Leu Pro Lys Ser Ser Asn Pro
            260                 265                 270 aag cgc att gag tcc aac ttc aag agc att gag ctc tcc gat gcc gac        864
Lys Arg Ile Glu Ser Asn Phe Lys Ser Ile Glu Leu Ser Asp Ala Asp
        275                 280                 285 ttt gaa gcc atc aat gcc gtt gcc aag ggt cgt cac ttc cgt ttc gtc        912
Phe Glu Ala Ile Asn Ala Val Ala Lys Gly Arg His Phe Arg Phe Val
    290                 295                 300 aac atg aag gat act ttc gga tat gat gtc tgg ccc gag gag acc gcc        960
Asn Met Lys Asp Thr Phe Gly Tyr Asp Val Trp Pro Glu Glu Thr Ala
305                 310                 315                 320 aag aac ctg tct gcg tgaatctcta cgaaattata a                            996
Lys Asn Leu Ser Ala
                325

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 29
cggatccgtt cacgcagaca ggttcttgg                                        29

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 30
gccatggcta tgtataaaga tttagaa                                          27

<210> SEQ ID NO 31

<400> SEQUENCE: 31

000

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 32
cggatccgtt atccgcgtcc tgc                                              23
```

-continued

```
<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 33
cggatccgag cgcccaatac gcaaaccg                                          28

<210> SEQ ID NO 34
<211> LENGTH: 385
<212> TYPE: PRT
<213> ORGANISM: Corynebacterium sp.

<400> SEQUENCE: 34
```

Met Lys Ala Ile Gln Tyr Thr Arg Ile Gly Ala Glu Pro Glu Leu Thr
 1               5                  10                  15

Glu Ile Pro Lys Pro Glu Pro Gly Pro Gly Glu Val Leu Leu Glu Val
             20                  25                  30

Thr Ala Ala Gly Val Cys His Ser Asp Asp Phe Ile Met Ser Leu Pro
         35                  40                  45

Glu Glu Gln Tyr Thr Tyr Gly Leu Pro Leu Thr Leu Gly His Glu Gly
     50                  55                  60

Ala Gly Lys Val Ala Val Gly Glu Gly Val Glu Gly Leu Asp Ile
 65                  70                  75                  80

Gly Thr Asn Val Val Tyr Gly Pro Trp Gly Cys Gly Asn Cys Trp
                 85                  90                  95

His Cys Ser Gln Gly Leu Glu Asn Tyr Cys Ser Arg Ala Gln Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Gly Gly Gly Asp
305                 310                 315                 320

-continued

```
Leu Gln Ser Arg Gln Arg Cys Arg Ser Val Ser Thr Thr Gly Cys Arg
            325                 330                 335
Asn Ala Gln Arg Pro Cys Gly Cys Gly Pro Trp Ser Val Val Pro Thr
            340                 345                 350
Ala Val Glu Arg Gln Arg Lys Asn Thr Asp Ala Arg Pro Asn Ser Ile
            355                 360                 365
Arg Pro Gly Ile Ser Val Arg Asn Ser Val Cys Ala Ser Cys Thr Pro
    370                 375                 380
Arg
385

<210> SEQ ID NO 35
<211> LENGTH: 1158
<212> TYPE: DNA
<213> ORGANISM: Corynebacterium sp.
<220> FEATURE:
<221> NAME/KEY: CDS
<222> LOCATION: (1)..(1155)

<400> SEQUENCE: 35
```

| | |
|---|---|
| atg aag gcg atc cag tac acg cga atc ggc gcg gaa ccc gaa ctc acg<br>Met Lys Ala Ile Gln Tyr Thr Arg Ile Gly Ala Glu Pro Glu Leu Thr<br>1                    5                    10                 15 | 48 |
| gag att ccc aaa ccc gag ccc ggt cca ggt gaa gtg ctc ctg gaa gtc<br>Glu Ile Pro Lys Pro Glu Pro Gly Pro Gly Glu Val Leu Leu Glu Val<br>                    20                    25                    30 | 96 |
| acc gct gct ggc gtc tgc cac tcg gac gac ttc atc atg agc ctg ccc<br>Thr Ala Ala Gly Val Cys His Ser Asp Asp Phe Ile Met Ser Leu Pro<br>              35                    40                    45 | 144 |
| gaa gag cag tac acc tac ggc ctt ccg ctc acg ctc ggc cac gaa ggc<br>Glu Glu Gln Tyr Thr Tyr Gly Leu Pro Leu Thr Leu Gly His Glu Gly<br>    50                    55                    60 | 192 |
| gca ggc aag gtc gcc gcc gtc ggc gag ggt gtc gaa ggt ctc gac atc<br>Ala Gly Lys Val Ala Ala Val Gly Glu Gly Val Glu Gly Leu Asp Ile<br>65                    70                    75                    80 | 240 |
| gga acc aat gtc gtc gtc tac ggg cct tgg ggt tgc ggc aac tgt tgg<br>Gly Thr Asn Val Val Val Tyr Gly Pro Trp Gly Cys Gly Asn Cys Trp<br>                    85                    90                    95 | 288 |
| cac tgc tca caa gga ctc gag aac tat tgc tct cgc gcc caa gaa ctc<br>His Cys Ser Gln Gly Leu Glu Asn Tyr Cys Ser Arg Ala Gln Glu Leu<br>                100                 105               110 | 336 |
| gga atc aat cct ccc ggt ctc ggt gca ccc ggc gcg ttg gcc gag ttc<br>Gly Ile Asn Pro Pro Gly Leu Gly Ala Pro Gly Ala Leu Ala Glu Phe<br>                115                 120               125 | 384 |
| atg atc gtc gat tct cct cgc cac ctt gtc ccg atc ggt gac ctc gac<br>Met Ile Val Asp Ser Pro Arg His Leu Val Pro Ile Gly Asp Leu Asp<br>130                  135                 140 | 432 |
| ccg gtc aag acg gtg ccg ctg acc gac gcc ggt ctg acg ccg tat cac<br>Pro Val Lys Thr Val Pro Leu Thr Asp Ala Gly Leu Thr Pro Tyr His<br>145                  150                 155               160 | 480 |
| gcg atc aag cgt tct ctg ccg aaa ctt cgc gga ggc tcg tac gcg gtt<br>Ala Ile Lys Arg Ser Leu Pro Lys Leu Arg Gly Gly Ser Tyr Ala Val<br>                165                 170               175 | 528 |
| gtc att ggt acc ggc ggt ctc ggc cac gtc gct att cag ctc ctc cgc<br>Val Ile Gly Thr Gly Gly Leu Gly His Val Ala Ile Gln Leu Leu Arg<br>                180                 185               190 | 576 |
| cac ctc tcg gcg gca acg gtc atc gct ttg gac gtg agc gcg gac aag<br>His Leu Ser Ala Ala Thr Val Ile Ala Leu Asp Val Ser Ala Asp Lys<br>                    195                 200               205 | 624 |
| ctc gaa ctg gca acc aag gta ggc gct cac gaa gtg gtt ctg tcc gac | 672 |

-continued

| | | |
|---|---|---|
| Leu Glu Leu Ala Thr Lys Val Gly Ala His Glu Val Val Leu Ser Asp<br>  210                 215                 220 | | |
| aag gac gcg gcc gag aac gtc cgc aag atc act gga agt caa ggc gcc<br>Lys Asp Ala Ala Glu Asn Val Arg Lys Ile Thr Gly Ser Gln Gly Ala<br>225                 230                 235                 240 | 720 | |
| gca ttg gtt ctc gac ttc gtc ggc tac cag ccc acc atc gac acc gcg<br>Ala Leu Val Leu Asp Phe Val Gly Tyr Gln Pro Thr Ile Asp Thr Ala<br>                245                 250                 255 | 768 | |
| atg gct gtc gcc ggc gtc gga tca gac gtc acg atc gtc ggg atc ggg<br>Met Ala Val Ala Gly Val Gly Ser Asp Val Thr Ile Val Gly Ile Gly<br>        260                 265                 270 | 816 | |
| gac ggc cag gcc cac gcc aaa gtc ggg ttc ttc caa agt cct tac gag<br>Asp Gly Gln Ala His Ala Lys Val Gly Phe Phe Gln Ser Pro Tyr Glu<br>275                 280                 285 | 864 | |
| gct tcg gtg aca gtt ccg tat tgg ggt gcc cgc aac gag ttg atc gaa<br>Ala Ser Val Thr Val Pro Tyr Trp Gly Ala Arg Asn Glu Leu Ile Glu<br>        290                 295                 300 | 912 | |
| ttg atc gac ctc gcc cac gcc ggc atc ttc gac atc ggc ggt gga gac<br>Leu Ile Asp Leu Ala His Ala Gly Ile Phe Asp Ile Gly Gly Gly Asp<br>305                 310                 315                 320 | 960 | |
| ctt cag tct cga caa cgg tgc cga agc gta tcg acg act ggc tgc cgg<br>Leu Gln Ser Arg Gln Arg Cys Arg Ser Val Ser Thr Thr Gly Cys Arg<br>                325                 330                 335 | 1008 | |
| aac gct cag cgg ccg tgc ggt tgt ggt ccc tgg tct gta gta ccg aca<br>Asn Ala Gln Arg Pro Cys Gly Cys Gly Pro Trp Ser Val Val Pro Thr<br>        340                 345                 350 | 1056 | |
| gcg gta gaa cga cag cgg aaa aac act gat gcc cgg ccg aat tcg att<br>Ala Val Glu Arg Gln Arg Lys Asn Thr Asp Ala Arg Pro Asn Ser Ile<br>355                 360                 365 | 1104 | |
| cgg ccg ggc atc agt gtc aga aat tcg gtg tgc gct agc tgc acg cct<br>Arg Pro Gly Ile Ser Val Arg Asn Ser Val Cys Ala Ser Cys Thr Pro<br>        370                 375                 380 | 1152 | |
| cga tga<br>Arg<br>385 | 1158 | |

<210> SEQ ID NO 36
<211> LENGTH: 261
<212> TYPE: PRT
<213> ORGANISM: Escherichia coli

<400> SEQUENCE: 36

Met Tyr Lys Asp Leu Glu Gly Lys Val Val Ile Thr Gly Ser Ser
 1               5                  10                  15

Thr Gly Leu Gly Lys Ala Met Ala Ile Arg Phe Ala Thr Glu Lys Ala
            20                  25                  30

Lys Val Val Asn Tyr Arg Ser Lys Glu Glu Ala Asn Ser Val
        35                  40                  45

Leu Glu Glu Ile Lys Lys Val Gly Gly Glu Ala Ile Ala Val Lys Gly
    50                  55                  60

Asp Val Thr Val Glu Ser Asp Val Ile Asn Leu Val Gln Ser Ala Ile
65                  70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

-continued

```
Lys Tyr Phe Val Glu Asn Asp Ile Lys Gly Thr Val Ile Asn Met Ser
    130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Glu Gln Arg Ala Asp
            195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Trp Ile Ser Thr Lys Leu
  1               5
```